(12) United States Patent
Itoh et al.

(10) Patent No.: US 8,097,697 B2
(45) Date of Patent: Jan. 17, 2012

(54) TUMOR ANTIGEN PROTEIN SART-3 AND TUMOR ANTIGEN PEPTIDES THEREOF

(75) Inventors: Kyogo Itoh, Miyaki-gun (JP); Masanobu Nakao, Okawa (JP)

(73) Assignee: Green Peptide Co., Ltd., Kurume-shi (JP)

( * ) Notice: Subject to any disclaimer, the term of this patent is extended or adjusted under 35 U.S.C. 154(b) by 0 days.

(21) Appl. No.: 13/109,976

(22) Filed: May 17, 2011

(65) Prior Publication Data

US 2011/0243974 A1  Oct. 6, 2011

Related U.S. Application Data

(62) Division of application No. 12/432,700, filed on Apr. 29, 2009, now Pat. No. 7,968,676, which is a division of application No. 10/781,659, filed on Feb. 20, 2004, now Pat. No. 7,541,428, and a division of application No. 09/763,985, filed as application No. PCT/JP99/04622 on Aug. 27, 1999, now abandoned.

(30) Foreign Application Priority Data

Aug. 28, 1998 (JP) .................................... 10-242660

(51) Int. Cl.
  *C07K 5/00* (2006.01)
  *A61K 39/00* (2006.01)
(52) U.S. Cl. ..................................... 530/300; 424/184.1
(58) Field of Classification Search .......................... None
See application file for complete search history.

(56) References Cited

U.S. PATENT DOCUMENTS

| | | | |
|---|---|---|---|
| 5,750,395 A | 5/1998 | Fikes et al. | |
| 2006/0035251 A1 | 2/2006 | Young et al. | |

FOREIGN PATENT DOCUMENTS

| | | |
|---|---|---|
| EP | 0911397 | 4/1999 |
| EP | 1033401 | 9/2000 |
| WO | WO-97/46676 A1 | 12/1997 |
| WO | WO-00/55174 | 9/2000 |

OTHER PUBLICATIONS

Toh at al., Cellular Immunology, vol. 177, Article No. CI971105, pp. 137-143, (1997).
Yang et al., Cancer Research, vol. 59, pp. 4056-4063, (1999).
Accession No. HSORF51, "Human mRNA for KIA0156 gene, complete cds.", Aug. 8, 1995, EMBL Database.
Accession No. AAGO1853, "Human Secreted protein, SEQ ID No. 5934.", Sep. 6, 2000, EMBL Database.
Shuchijo at al., "A Gene Encoding Antigenic Peptides of Human Squamous Cell Carcinoma Recognized by Cytotoxic T lymphocytes" J. Exp. Med, vol. 187, No. 3, pp. 277-288, (Feb. 2, 1998).
Gohara "Histocompatibility Leukocyte Antigen-A2402-restricted Cytotoxic T Lymphoctyes Recognizing Adenocarinoma in Tumor-infiltrating Lymphocytes of Patients with Colon Cancer" Jpn. J. Cancer Res., vol. 88, No. 2, pp. 198-204, (Feb. 1997).
Nagase "Prediction of the Coding sequences of Unidentified Human Genes. IV. The Coding Sequence of 40 New Genes (KIAA0121-KIAA0160) Deduced by Analysis of cDNA Clones from Human Cell Line KG-1" J. Clin. Invest., vol. 2, No. 4, pp. 167-174 (Aug. 1995).
Yotnda "Cytotoxic T cell Response Against the Chimeric ETV6-AML1 Protein in Childhood Acute Lymphblastic Leukemia" J. Clin. Invest., vol. 102, No. 2, pp. 455-462, (Jul. 1998).
Takahashi "Recognition of gp43 Tumor-Associated Antigen Peptide by both HLA-A2 Restricted CTL Lines and Antibodies from Melanoma Patients" Cellular Immunology, col. 178, No. 2, pp. 162-171, (Jun. 15, 1997).
Rosenberg et al., "Treatment of Patients with Metastatic Melanoma with Autologous Tumor-Infiltrating Lymphocytes and Interleukin 2" ; J. of the Natl. Cancer Inst., vol. 86, No. 15, (Aug. 1994).
Rammensee et al., "MHC Ligands and Peptide Motifis: First Listing"; Immunogenetics, vol. 41, pp. 178-228 (1995).
Kubo et al., "Definition of Specific Peptide Motifs for Four Major HLA-A Alleles" ; J. of Immunology, vol. 152, pp. 3913-3924 (1994).
Kondo at al., "Prominent Roles of Secondary Anchor Residues in Peptide Binding to HLA-A24 Human Class I Molecules" ; J. of Immunology, vol. 155, pp. 4307-4312 (1995).
Sudo et al., "Differences in MHC Class I Self peptide Repertoires among HLA-A2 Subtypes" ; The J. of Immunology, vol. 155, pp. 4749-4756 (1995).
Rivoltini at al., "Induction of Tumor-Reactive CTL from peripheral Blood and Tumor-Infiltrating Lymphocytes of Melanoma Patients by in Vitro Stimulation with an Immunodominant Peptide of the Human Melanoma Antigen MART-1"; The J. of Immunology, vol. 154, pp. 2257-2265 (1995).
Kharkevitch et al., "Characterization of Autologous Tumor-Specific T-Helper 2 Cells in Tumor-Infiltrating Lymphoctyes from a Patient with Metastatic Melanoma" ; Int. J. Cancer, col. 58, pp. 317-323 (1994).
Van Tsai et al. "Identification of Subdominant CTL Epitopes of the GP100 Melanoma-Associated Tumor Antigen by Primary in Vitro Immunization with Peptide-Pulsed Dendritic Cells" ; The J. of Immunology, vol. 158, pp. 1796-1802 (1997).
Altman et al., "Phenotypic Analysis of Antigen-Specific T Lymphocytes" ; Science, col. 274, pp. 94-96 (Oct. 1996).
Nakao et al., "HLA A2601-restricted CTLs Recognize a peptide Antigen Expressed on Squamous Cell Carcinoma" ; Cancer Research, col. 55, pp. 4248-4252 (Oct. 1995).
Thompsen et al., "Delivery of Multiple CD8 Cytotoxic T Cell Epitopes by DNA Vaccination"; The J. of immunology, col. 160, pp. 1717-1723 (1998).
KIAA0156 (Genbank Accession No. D63879), (Jul. 10, 1997).
HLA-A2 cDNA (Genbank Accession No. M84379), (Jan. 7, 1995).
Crystal, R.G. Science. vol. 270, pp. 404-410, (Oct. 1995).

(Continued)

Primary Examiner — Misook Yu
Assistant Examiner — Lei Yao
(74) Attorney, Agent, or Firm — Birch, Stewart, Kolasch & Birch, LLP

(57) ABSTRACT

A novel tumor antigen protein and gene therefor, tumor antigen peptides derived from said tumor antigen protein or derivatives thereof as well as medicaments, prophylactics, or diagnostics for tumors using such tumor substances in vitro or in vitro are provided.

6 Claims, No Drawings

OTHER PUBLICATIONS

Tait et al., Clin. Canc. Res., vol. 5, pp. 1708-1714, (Jul. 1999).
Gura, Science, vol. 278, pp. 1041-1042, (1997).
Miyagi et al., Clinical Cancer Res., vol. 7, pp. 3950-3962, (2001).
Kurshid et al., Analytical Biochemistry, vol. 208, pp. 138, (1993) Abstract.
Gaiger et al., Blood, vol. 96, pp. 1480-1489, (2000).
Boon, Adv. Can. Res., vol. 58, pp. 177-210, (1992).
Spitler, Cancer Biotherapy, vol. 10, pp. 1-3, (1996).
Ezzel. J. NIH Res., vol. 7, pp. 46-49, (1995).
Nagase et al., DNA Res., vol. 2, pp. 167-174, supplement 199-210, (1995).
Sambrook et al., Molecular Cloning, A Laboratory Manual, Chapters 3 and 12 (1989).
Kausch et al., Plan Physiol, vol. 107 pp. 669-670, 1995.
Yang et al., Cancer Research, vol. 59, pp. 4056-1063, 1999.
Abbas et al., Cellular and Molecular Immunology, 4th edition. 2000, p. 71-72.
Nagase et al., DNA Res, 2:167-174, 1995.

TUMOR ANTIGEN PROTEIN SART-3 AND TUMOR ANTIGEN PEPTIDES THEREOF

RELATED APPLICATIONS

This application claims priority under 35 USC §120 as a Divisional of co-pending application Ser. No. 12/432,700, filed Apr. 29, 2009 and issued Jun. 28, 2011 as U.S. Pat. No. 7,968,676, which is a Divisional of application Ser. No. 10/781,659, filed on Feb. 20, 2004 and issued Jun. 2, 2009 as U.S. Pat. No. 7,541,428, which is a Divisional of application Ser. No. 09/763,985, filed on Feb. 28, 2001 and now abandoned, which in turn is the National Stage of International Application No. PCT/JP1999/04622 filed on Aug. 27, 1999. This application also claims priority of Application No. 242660/1998 filed in Japan on Aug. 28, 1998, under 35 U.S.C. §119. The entire contents of each of the above applications is hereby incorporated by reference.

TECHNICAL FIELD

The present invention relates to the novel tumor antigen protein, and tumor antigen peptides thereof. More particularly, it relates to the novel tumor antigen protein and the gene thereof, tumor antigen peptides derived from the tumor antigen protein, and derivatives of their substances, as well as to medicaments, prophylactics, or diagnostics for tumors that utilize in vivo or in vitro such tumor antigen protein, genes, tumor antigen peptides, or derivatives thereof.

BACKGROUND ART

It is known that immune system, particularly T cells, plays an important role in tumor elimination by a living body. Indeed, infiltration of lymphocytes exhibiting cytotoxic effects on tumor cells in human tumor foci has been observed (*Arch. Surg.*, 126:200, 1990), and cytotoxic T lymphocytes (CTLs) recognizing autologous tumor cells have been isolated from melanomas without great difficulties (e.g., *Immunol. Today*, 8:385, 1987; *J. Immunol.*, 138:989, 1987; and *Int. J. Cancer*, 52:52, 1992). In addition, the results of clinical treatment of melanomas by transfer of the CTLs recognizing autologous tumor cells also suggest the importance of T cells in tumor elimination (*J. Natl. Cancer. Inst.*, 86:1159, 1994).

Although it had long been unknown about target molecules for CTLs attacking autologous tumor cells, the recent advance in immunology and molecular biology gradually began elucidating such target molecules. Specifically, it has been found that CTL, using the T cell receptors (TCRs), recognizes a complex between a peptide, called tumor antigen peptide, and a major histocompatibility complex class I antigen (MHC class I antigen, and in the case of human, referred to as HLA antigen), and thereby attacks autologous tumor cells.

Tumor antigen peptides are generated by degradation of tumor antigen proteins, which are proteins specific for tumors, in cells with proteasomes, which proteins are intracellularly synthesized. The tumor antigen peptides thus generated bind to MHC class I antigens (HLA antigens) in endoplasmic reticulum to form complexes, and the complexes are transported to the cell surface to be presented as an antigen. A tumor-specific CTL recognizes the complex presented as an antigen, and exhibits anti-tumor effects through its cytotoxic action or production of lymphokines. As a consequence of elucidation of a series of the actions, it has become possible to treat tumors by using tumor antigen proteins or tumor antigen peptides as so-called cancer vaccines to enhance tumor-specific CTLs in the body of a tumor patient.

As a tumor antigen protein, T. Boon et al. identified a protein named MAGE from human melanoma cells for the first time in 1991 (*Science*, 254:1643, 1991). Subsequently, several additional tumor antigen proteins have been identified mainly from melanoma cells. Examples of melanoma antigens that have been identified are melanosomal proteins such as a melanocytic tissue-specific protein, gp100 (*J. Exp. Med.*, 179:1005, 1994), MART-1 (*Proc. Natl. Acad. Sci. USA*, 91:3515, 1994), and tyrosinase (*J. Exp. Med.*, 178:489, 1993); MEGE-related proteins that are expressed not only on melanomas but also on various cancer cells and normal testicular cells (*J. Exp. Med.*, 179:921, 1994); β-catenin having a tumor-specific amino acid mutation (*J. Exp. Med.*, 183:1185, 1996); and CDK4 (*Science*, 269:1281, 1995). Tumor antigen proteins other than those from melanomas have also been identified, including products of oncogenes such as HER2-neu (*J. Exp. Med.*, 181:2109, 1995) and p53 (variant) (*Proc. Natl. Acad. Sci. USA*, 93:14704, 1996); tumor markers such as CEA (*J. Natl. Cancer Inst.*, 87:982, 1995) and PSA (*J. Natl. Cancer Inst.*, 89:293, 1997); and viral proteins such as HPV (*J. Immunol.*, 154:5934, 1995) and EBV (*Int. Immunol.*, 7:653, 1995). Detailed descriptions of these substances can be found in published reviews (e.g. *Immunol. Today*, 18:267, 1997; *J. Exp. Med.*, 183:725, 1996; and *Curr. Opin. Immunol.*, 8:628, 1996).

In applications of a tumor antigen protein or a tumor antigen peptide to treatment or diagnosis of tumors, it is important to identify a tumor antigen that can be widely applied to squamous cell carcinomas such as esophageal and lung cancers that occur at a much higher incidence compared to melanomas. In this relation, the present inventors conducted cloning of a gene encoding a novel tumor antigen protein from squamous cell carcinoma cells derived from esophageal cancer, and identified for the first time from the tumor cell other than melanomas several tumor antigen peptides that are bound to and presented on HLA antigens of which HLA types are HLA-A24 or HLA-A26 (*J. Exp. Med.*, 187:277, 1998; International Patent Publication WO 97/46676).

When these tumor antigen peptides are clinically applied in practice, it may be desirable to use two or more different tumor antigen peptides rather than to use merely one peptide. That is to say, taking into consideration the facts that all cancer cells do not express an identical tumor antigen in common and that two or more different tumor antigen peptides are presented on a single cancer cell, a treatment using two or more different tumor antigen peptides is believed to be more effective. Indeed, in the case of melanoma, development of cocktail formulations comprising two or more peptides has been attempted, since a single peptide derived from a tumor antigen failed to exhibit adequate effects (*Int. J. Cancer*, 66:162, 1996; and *Int. J. Cancer*, 67:54, 1996). Under such circumstances, it is being required to identify novel tumor antigen proteins and tumor antigen peptides that can be widely applied to squamous cell carcinomas that occur at a higher incidence.

DISCLOSURE OF THE INVENTION

The present invention aims to provide the novel tumor antigen protein and tumor antigen peptides. Particularly, it aims to provide the novel tumor antigen protein and gene thereof, tumor antigen peptides derived from the tumor antigen protein, and derivatives of their substances, as well as to medicaments, prophylactics, or diagnostics for tumors that utilize in vivo or in vitro such tumor antigen protein, genes, tumor antigen peptides, or derivatives thereof. The tumor antigen peptides of the present invention include a tumor antigen peptide that is bound to and presented on HLA-A24 that is the HLA antigen carried by about 60% of the Japanese people and a tumor antigen peptide that is bound to and presented on HLA-A2 carried by about 40% of the Japanese and the Caucasians, and, therefore, it can be applied to many patients. Further, the tumor antigen peptides of the present invention may be also applied to squamous cell carcinomas or the like that is recognized most frequently as an etiologic cancer in human, and are expected to have utilities as novel anti-tumor medicaments. It is known that the squamous cell carcinoma on esophageal or lung cancer among the squamous cell carcinomas tends to relatively exhibit a resistance to the current chemotherapy and radiotherapy. In this respect, the development of the tumor antigen peptides of the present invention is desired.

In order to obtain novel tumor antigen protein and tumor antigen peptides, the present inventors made the following attempts.

First of all, the present inventors prepared a cDNA library from esophageal cancer cell line KE-4 (FERM BP-5955), and doubly transfected fibroblast cell line VA-13 (RIKEN CELL BANK, The Institute of Physical and Chemical Research) with a recombinant plasmid of the library and a recombinant plasmid containing cDNA of HLA-A2402 (one type of HLA-A24). The resulting transfectants were treated with KE-4CTL (FERM BP-5954) that is directed to KE-4, and the amount of produced IFN-γ was measured to determine whether or not KE-4CTL was activated. As a result of such extensive screening repeatedly conducted, the present inventors finally succeeded in cloning one gene encoding a tumor antigen protein although we did not assure that the screening resulted in a novel and useful tumor antigen protein. The inventors named the tumor antigen protein encoded by the gene "SART-3". Comparing the base sequence of SART-3 with known sequences revealed that said base sequence of SART-3 was a novel base sequence that is different from the KIAA0156 gene registered as Accession No. D63879 at GenBank database in terms of a single base, which function has not been demonstrated.

Further, the present inventors identified tumor antigen peptide portions residing in the amino acid sequence of SART-3 that are bound to and presented on HLA-A24 and HLA-A2, and demonstrated that such peptides have activity as a tumor antigen peptide.

The present invention has been completed on the basis of the findings as described above.

Thus, the present invention relates to:

(1) A DNA encoding a protein consisting of an amino acid sequence shown in SEQ ID NO: 2, or a protein variant consisting of an amino acid sequence containing substitution, deletion, and/or addition of one or more amino acid residues of SEQ ID NO: 2, provided that the protein and the protein variant give rise to tumor antigen peptides that are capable of binding to an HLA antigen and being recognized by cytotoxic T lymphocytes;

(2) A DNA consisting of a base sequence shown in SEQ ID NO: 1, or a DNA variant that hybridizes to the DNA under a stringent condition, provided that a protein produced and expressed by the DNA or the DNA variant gives rise to tumor antigen peptides that are capable of binding to an HLA antigen and being recognized by cytotoxic T lymphocytes;

(3) An expression plasmid that contains the DNA of the above (1) or (2);

(4) A transformant that is transformed with the expression plasmid of the above (3);

(5) A process for producing a recombinant protein, which comprises culturing the transformant of the above (4), and recovering the expressed recombinant protein;

(6) A tumor antigen protein that is encoded by the DNA of the above (1) or (2), or is produced by the process of the above (5);

(7) A pharmaceutical composition that comprises as an active ingredient the DNA of the above (1) or (2), or the protein of the above (6);

(8) A pharmaceutical composition for treating or preventing tumors, which comprises as an active ingredient the DNA of the above (1) or (2), or the protein of the above (6);

(9) A tumor antigen peptide that is a partial peptide derived from the protein of the above (6), and that is capable of binding to an HLA antigen and being recognized by cytotoxic T lymphocytes, or a derivative thereof having the functionally equivalent properties;

(10) The tumor antigen peptide of the above (9) wherein the HLA antigen is HLA-A24 or HLA-A2, or a derivative thereof having the functionally equivalent properties;

(11) The tumor antigen peptide of the above (10), which comprises a sequence selected from all or part of an amino acid sequence shown in any one of SEQ ID NOs: 3-52, or a derivative thereof having the functionally equivalent properties;

(12) The tumor antigen peptide of the above (11), which comprises a sequence selected from all or part of an amino acid sequence shown in any one of SEQ ID NOs: 3-9 and 25-29, or a derivative thereof having the functionally equivalent properties;

(13) The tumor antigen peptide derivative of the above (11), which comprises a sequence selected from all or part of an amino acid sequence wherein the amino acid residue at position 2 and/or the C-terminus in the amino acid sequence shown in any one of SEQ ID NOs: 3-52 is substituted by another amino acid residue;

(14) The tumor antigen peptide derivative of the above (13), which comprises a sequence selected from all or part of an amino acid sequence wherein the amino acid residue at position 2 and/or the C-terminus in the amino acid sequence shown in any one of SEQ ID NOs: 3-9 and 25-29 is substituted by another amino acid residue;

(15) The tumor antigen peptide derivative of the above (13), which comprises a sequence selected from all or part of an amino acid sequence wherein the amino acid residue at position 2 in the amino acid sequence shown in any one of SEQ ID NOs: 3-24 is substituted by tyrosine, phenylalanine, methionine, or tryptophan, and/or the amino acid residue at the C-terminus is substituted by phenylalanine, leucine, isoleucine, tryptophan, or methionine;

(16) The tumor antigen peptide derivative of the above (13), which comprises a sequence selected from all or part of an amino acid sequence wherein the amino acid residue at position 2 in the amino acid sequence shown in any one of SEQ ID NOs: 25-52 is substituted by leucine, methionine, valine, isoleucine, or glutamine, and/or the amino acid residue at the C-terminus is substituted by valine or leucine;

(17) The tumor antigen peptide derivative of the above (14), which comprises a sequence selected from all or part of the amino acid sequence shown in any one of SEQ ID NOs: 53-64;

(18) A pharmaceutical composition for treating or preventing tumors, which comprises as an active ingredient at least one of substances selected from the tumor antigen peptides and derivatives thereof according to any one of the above (9) to (17);

(19) A recombinant DNA comprising at least one of DNAs that encode the tumor antigen peptides or derivatives thereof according to any one of the above (9) to (17);

(20) A recombinant polypeptide obtainable by expressing the recombinant DNA of the above (19);

(21) A pharmaceutical composition for treating or preventing tumors, which comprises as an active ingredient the recombinant DNA of the above (19) or the recombinant polypeptide of the above (20);

(22) An antibody that specifically binds to any one of the tumor antigen protein of the above (6), and the tumor antigen peptide or the derivative thereof according to any one of the above (9) to (17);

(23) An antigen-presenting cell wherein a complex between an HLA antigen and the tumor antigen peptide or the derivative thereof according to any one of the above (9) to (17) is presented on the surface of a cell having antigen-presenting ability, which cell is isolated from a tumor patient;

(24) An antigen-presenting cell on which a complex between an HLA antigen and a tumor antigen peptide or a derivative thereof is presented, said antigen-presenting cell being obtainable by allowing a cell having antigen-presenting ability isolated from a tumor patient to be incorporated with the DNA of the above (1) or (2), the tumor antigen protein of the above (6), the recombinant DNA of the above (19), or the recombinant polypeptide of the above (20);

(25) A pharmaceutical composition for treating tumors, which comprises as an active ingredient the antigen-presenting cell of the above (23) or (24);

(26) A cytotoxic T lymphocyte that specifically recognizes a complex between an HLA antigen and the tumor antigen peptide or derivative thereof according to any one of the above (9) to (17);

(27) A cytotoxic T lymphocyte that specifically recognizes a complex between an HLA antigen and a tumor antigen peptide or derivative thereof, which complex is presented on the antigen-presenting cell of the above (23) or (24);

(28) A pharmaceutical composition for treating tumors, which comprises as an active ingredient the cytotoxic T lymphocyte of the above (26) or (27);

(29) A diagnostic agent for tumors, which comprises the tumor antigen peptide or derivative thereof according to any one of the above (9) to (17), the protein of the above (6), or the recombinant polypeptide of the above (20);

(30) Cytotoxic T lymphocyte OK-CTL, of which the deposit number is FERM BP-6818; and

(31) A method for identifying tumor antigen proteins or tumor antigen peptides, which comprises using OK-CTL of the above (30).

The DNAs of the present invention encode novel tumor antigen proteins, and specific examples of the DNAs include a DNA encoding SART-3 protein consisting of an amino acid sequence shown in SEQ ID NO: 2, or a protein variant consisting of an amino acid sequence containing substitution, deletion, and/or addition of one or more amino acid residues of the amino acid sequence of SART-3, provided that the protein and the protein variant give rise to tumor antigen peptides that are capable of binding to an HLA antigen and being recognized by cytotoxic T lymphocytes; or a DNA of SART-3 consisting of a base sequence shown in SEQ ID NO: 1, or a DNA variant that hybridizes to the DNA of SART-3 under a stringent condition, provided that a protein produced and expressed by the DNA and the DNA variant gives rise to tumor antigen peptides that are capable of binding to an HLA antigen and being recognized by cytotoxic T lymphocytes. The DNA of the present invention is further described hereinafter following the order established above.

1) DNA Encoding SART-3

"DNA encoding a protein consisting of an amino acid sequence shown in SEQ ID NO: 2" and "a DNA consisting of a base sequence shown in SEQ ID NO: 1" among the DNAs described above refers to a DNA encoding tumor antigen protein SART-3 of the present invention. The DNA may be cloned in accordance with the process described in Examples hereinafter. Further, the cloning of the DNA may be also conducted by, for example, screening a cDNA library derived from cell lines such as esophageal cancer cell line KE-4 (FERM BP-5955) using an appropriate portion of the base sequence disclosed in GenBank Accession No. D63879 or shown in SEQ ID NO: 1 in the present specification as a probe for hybridization or a PCR primer. It would be ready for those skilled in the art to achieve such cloning in accordance with Molecular Cloning 2nd Edt. Cold Spring Harbor Laboratory Press (1989), for example.

2) DNA Encoding a Modified Protein of SART-3 or Allelic Variant Thereof

"DNA encoding a protein variant consisting of an amino acid sequence containing substitution, deletion, and/or addition of one or more amino acid residues of the amino acid sequence of SART-3" among the DNAs described above refers to a DNA that encodes a so-called modified protein, which is artificially prepared, or proteins such as an allelic variant existing in a living body. The DNA encoding such protein variants may be prepared by diverse methods such as site-directed mutagenesis and PCR technique that are described in Molecular Cloning: A Laboratory Manual 2nd Edt. vols. 1-3, Cold Spring Harbor Laboratory Press (1989). Number of amino acid residue to be substituted, deleted and/or added should be in a range that enables the substitution, deletion, and/or addition in accordance with the well-known methods such as site-directed mutagenesis as shown above.

3) DNA that Hybridizes to the DNA of SART-3 Under a Stringent Condition

"DNA variant that hybridizes to the DNA of SART-3 under a stringent condition" among the DNAs described above refers to a DNA that hybridizes to human SART-3 cDNA consisting of the base sequence shown in SEQ ID NO: 1 under a stringent condition, including SART-3 DNAs from all of vertebrate such as rat and mouse, and DNAs encoding a partial protein of SART-3.

The term "stringent condition" refers to a condition such that a hybridization is conducted in a solution containing 6×SSC (20×SSC represents 333 mM Sodium citrate, 333 mM NaCl), 0.5% SDS and 50% formamide at 42° C., and then the hybridized products are washed in a solution of 0.1×SSC, 0.5% SDS at 68° C., or to conditions as described in Nakayama, et al., *Bio-Jikken-Illustrated*, vol. 2, "Idenshi-Kaiseki-No-Kiso (A Basis for Gene Analysis)", pp. 148-151, Shujunsha, 1995.

The DNA variants are cloned by diverse processes such as hybridization to the DNA shown in SEQ ID NO: 1. Particular procedures for the processes such as production of cDNA library, hybridization, selection of positive colony, and determination of base sequence are well-known, and may be conducted consulting Molecular Cloning as shown above. Probes useful for the hybridization includes a DNA comprising a base sequence described in SEQ ID NO: 1.

Among the DNAs as described above 1) to 3), a DNA having an ability to generate a tumor antigen peptide that is capable of binding to an HLA antigen and being recognized by CTLs, and that is derived from a protein produced by the expression of the DNA via intracellular degradation, constitutes the DNA encoding tumor antigen protein of the present invention, namely, the DNA of the present invention. Particularly, the DNAs of the present invention are those that generate such peptide fragment as a partial peptide consisting of a part of an amino acid sequence of a protein produced by the expression of said DNA, said peptide being capable of binding to an HLA antigen, and inducing production of cytotoxic actions and cytokines from CTLs specific for the complex between the peptide and the HLA antigen that bind to the complex presenting on the cell surface.

Determination whether or not a candidate DNA may be a DNA encoding a tumor antigen protein may be achieved for example by the following method.

An expression plasmid containing a candidate DNA and an expression plasmid containing a DNA encoding an HLA antigen are doubly transfected into fibroblast VA-13 (RIKEN CELL BANK, The Institute of Physical and Chemical Research) or COS-7 (ATCC CRL 1651) derived from African green monkey kidney. The transfection may be achieved, for example, by the Lipofectin method using Lipofectamine reagent (GIBCO BRL). Subsequently, a tumor-responsive CTL that is restricted to the particular HLA antigen used is added to act on the transfectants, and then the amount of various cytokines (for example, IFN-γ) produced by said CTL in response to the transfectants may be measured, for example, by ELISA to determine whether or not the candidate DNA is a DNA of the present invention. In this context, since SART-3 contains HLA-A24- or HLA-A2-restricted tumor antigen peptide portions, HLA-A24 cDNA (*Cancer Res.*, 55:4248-4252 (1995); Genbank Accession No. M64740) and HLA-A2 cDNA (Genbank Accession No. M84379) may be used as the above DNA encoding the HLA antigen, whereas those CTLs that are prepared from human peripheral blood lymphocytes as well as HLA-A24-restricted CTLs such as KE-4CTL (FERM BP-5954) or HLA-A2-restricted CTLs such as OK-CTL (FERM BP-6818) may be used as the above CTL.

The DNA of the present invention as described above can be used as an active ingredient in a medicament or a pharmaceutical composition. In accordance with "pharmaceutical composition" that comprises the DNA of the present invention as an active ingredient, administration of the DNA of the present invention to a tumor patient makes treatment or prevention of tumors possible.

By administering a DNA of the present invention incorporated into an expression vector to a tumor patient according to the following method, the tumor antigen protein is highly expressed in antigen-presenting cells. Tumor antigen peptides that are subsequently generated by intracellular degradation bind to HLA antigen to form complexes, and the complexes are densely presented on the antigen-presenting cell surface. As a result, CTLs specific for tumors efficiently proliferate in the body, and destroy tumor cells. In this way, treatment or prevention of tumors is achieved.

Administration and introduction of the DNA of the present invention into cells may be achieved using viral vectors or according to any one of other procedures (*Nikkei-Science*, April, 1994, pp. 20-45; *Gekkan-Yakuji*, 36(1), 23-48 (1994); *Jikken-Igaku-Zokan*, 12(15), 1994, and references cited therein).

Examples of the methods using viral vectors include methods in which DNA of the present invention is incorporated into DNA or RNA virus such as retrovirus, adenovirus, adeno-associated virus, herpesvirus, vaccinia virus, poxvirus, poliovirus, or Sindbis virus, and introduced into cells. Among these methods, those using retrovirus, adenovirus, adeno-associated virus, or vaccinia virus are particularly preferred.

Other methods include those in which expression plasmids are directly injected intramuscularly (DNA vaccination), liposome method, Lipofectin method, microinjection, calcium phosphate method, and electroporation, and DNA vaccination and liposome method is particularly preferred.

In order to allow a DNA of the present invention to act as a medicament in practice, there are an in vivo method in which DNA is directly introduced into the body, and an ex vivo method in which certain cells are removed from human, and after introducing DNA into said cells extracorporeally, the cells are reintroduced into the body (*Nikkei-Science*, April, 1994, pp. 20-45; *Gekkan-Yakuji*, 36(1), 23-48 (1994); *Jikkenn-Igaku-Zokan*, 12(15), 1994; and references cited therein). An in vivo method is more preferred.

In case of in vivo methods, the DNA may be administered by any appropriate route depending on the disease and symptoms to be treated and other factors. For example, it may be administered via intravenous, intraarterial, subcutaneous, intracutaneous, intramuscular route, or the like. In the case of in vivo methods, the compositions may be administered in various dosage forms such as solution, and are typically formulated, for example, in the form of injection containing DNA of the present invention as an active ingredient, to which conventional carriers may also be added, if necessary. If a DNA of the present invention is included in liposomes or membrane-fused liposomes (such as Sendai virus (HVJ)-liposomes), the compositions may be in the form of liposome formulations such as suspension, frozen drug, centrifugally-concentrated frozen drug, or the like.

Although the amount of a DNA of the present invention in such formulations may vary depending on the disease to be treated, the age and the weight of the patient, and the like, it is typical to administer 0.0001 mg-100 mg, preferably 0.001 mg-10 mg, of a DNA of the present invention every several days to every several months.

In the invention, the term "protein" refers to a protein encoded by the various DNAs of the present invention as described above, which has an ability as tumor antigen protein to give rise to tumor antigen peptides via intracellular degradation that are capable of binding to an HLA antigen and being recognized by CTLs. Specific examples of the proteins include SART-3 comprising an amino acid sequence shown in SEQ ID NO: 2. The proteins of the present invention may be produced in large scale using the DNA of the present invention as described above.

Production of tumor antigen proteins by expressing the DNA of the present invention may be achieved in accordance with many publications and references such as "Molecular Cloning" mentioned above. Particularly, an expression plasmid that replicates and functions in host cells is constructed by incorporating a DNA of the present invention into an appropriate expression vector (e.g., pSV-SPORT1, pCR3). Subsequently, the expression plasmid is introduced into appropriate host cells to obtain transformants. Examples of host cells include those of prokaryotes such as *Escherichia coli*, unicellular eukaryotes such as yeast, and cells derived from multicellular eukaryotes such as insects or animals. Gene transfer into host cells may be achieved by conventional methods such as calcium phosphate method, DEAE-dextran method, electric pulse method, Lipofectin method, or the like. Desired proteins are produced by culturing the transformants in appropriate medium. The tumor antigen proteins thus obtained may be isolated and purified according to standard biochemical procedures.

It can be demonstrated whether or not a tumor antigen protein of the present invention has certain activity by, as described above, expressing the DNA of the present invention within cells to produce the protein of the present invention, and determining if the peptide fragment generated by intraellular degradation of said protein has the activity as a tumor antigen peptide. In case of using the tumor antigen protein as it is, the measurement for the activity can be achieved by allowing the protein to be incorporated into the phagocytes such as macrophage so as to generate peptide fragments in cells, and then contacting CTLs to complexes between the peptide fragments and HLA antigen, followed by measuring the amount of various cytokines (for example, IFN-γ) produced by the CTLs in response to the complexes.

The protein of the present invention as described above can be also used as an active ingredient in medicament or a pharmaceutical composition. In accordance with "pharmaceutical composition" that comprises the protein of the present invention as an active ingredient, administration of the protein of the present invention makes treatment or prevention of tumors possible, for example. When administered to a tumor patient, the protein of the present invention is introduced into antigen-presenting cells. Tumor antigen peptides that are subsequently generated by intracellular degradation bind to HLA antigen to form complexes, and the complexes are presented on the cell surface. CTLs specific for the complex efficiently proliferate in the body, and destroy tumor cells. In this way, treatment or prevention of tumors is achieved.

Pharmaceutical compositions comprising the tumor antigen protein of the present invention may be administered together with an adjuvant in order to effectively establish the cellular immunity, or may be administered in a particulate dosage form. For such purpose, those adjuvants described in the literature (Clin. Microbiol. Rev., 7:277-289, 1994) are applicable. In addition, liposomal preparations, particulate preparations in which the ingredient is bound to beads having a diameter of several μm, or preparations in which the ingredient is attached to lipids are also possible. Administration may be achieved, for example, intradermally, hypodermically, or by intravenous injection. Although the amount of a tumor antigen protein of the present invention in such formulations may vary depending on the disease to be treated, the age and the weight of the patient, and the like, it is typical to administer 0.0001 mg-1000 mg, preferably 0.001 mg-100 mg, more preferably 0.01 mg-10 mg of a tumor antigen protein of the present invention every several days to every several months.

In the present invention, the term "tumor antigen peptide" refers to a partial peptide that consists of a part of the tumor antigen protein of the present invention and is capable of binding to an HLA antigen and being recognized by CTL. Accordingly, any peptide falls within the scope of the tumor antigen peptide of the present invention, regardless of its length or its position in the amino acid sequence of the present protein, as long as the peptide consists of a part of the amino acid sequence of the present protein and a complex between said peptide and an HLA antigen is capable of being recognized by CTL. Such tumor antigen peptides of the present invention can be identified by synthesizing a candidate peptide which consists of a part of the tumor antigen protein of the present invention and conducting an assay for determining whether or not a complex between the candidate peptide and an HLA antigen is recognized by CTL, in other words, whether or not the candidate peptide has the activity as a tumor antigen peptide.

In this connection, synthesis of peptides may be conducted according to a method usually used in peptide chemistry. Examples of such known methods are those described in the literatures including "Peptide Synthesis", Interscience, New York, 1966; "The Proteins", vol. 2, Academic Press Inc., New York, 1976; "Pepuchido-Gosei", Maruzen Co. Ltd., 1975; "Pepuchido-Gosei-no-Kiso-to-Jikkenn", Maruzen Co. Ltd., 1985; and "Iyakuhin-no-Kaihatu, Zoku, vol. 14, Peputido-Gosei", Hirokawa Shoten, 1991.

Next, methods for identifying tumor antigen peptides of the present invention are further described below.

The respective sequence rules (motifs) of antigen peptides that are bound to and presented on the following HLA types have been known; HLA-A1, -A0201, -A0204, -A0205, -A0206, -A0207, -A11, -A24, -A31, -A6801, -B7, -B8, -B2705, -B37, -Cw0401, and -Cw0602 (see, e.g., *Immunogenetics*, 41:178, 1995). Regarding the motif for HLA-A24, for example, it is known that in the sequence of peptides consisting of 8 to 11 amino acids, the amino acid at position 2 is tyrosine, phenylalanine, methionine, or tryptophan, and the amino acid at the C-terminus is phenylalanine, leucine, isoleucine, tryptophan, or methionine (*J. Immunol.*, 152:3913, 1994; *Immunogenetics*, 41:178, 1995; *J. Immunol.*, 155:4307, 1994). Likewise, the motifs shown in the following Table 1 are known for HLA-A2 (*Immunogenetics*, 41:178, 1995; *J. Immunol.*, 155:4749, 1995).

TABLE 1

| Type of HLA-A2 | Amino acid at the second position from N-terminus | Amino acid at C-terminus |
|---|---|---|
| HLA-A0201 | L, M | V, L |
| HLA-A0204 | L | L |
| HLA-A0205 | V, L, I, M | L |
| HLA-A0206 | V, Q | V, L |
| HLA-A0207 | L | L |

(the peptides are 8-11 amino acids in length)

In addition, any peptide sequence expected to be capable of binding to HLA antigens may be searched on the internet using the BIMAS software of NIH.

By analysis of antigen peptides bound to various HLA molecules, it has been shown that the length of the peptides is usually about 8 to 14 amino acids long, although antigen peptides of 14 or more amino acids in length are also observed for HLA-DR, -DP, and -DQ (*Immunogenetics*, 41:178, 1995).

It is easy to select peptide portions involved in such motifs from the amino acid sequence of the protein of the present invention. Such peptide portions involved in the above motif structures can be easily selected by inspecting the amino acid sequence of tumor antigen protein SART-3 (SEQ ID NO: 2). Further, it is easy to select any sequence expected to be capable of binding to HLA antigens by search on internet as shown above. Tumor antigen peptides of the present invention can be identified by synthesizing candidate peptides thus selected according to the method described above and conducting an assay for determining whether or not a complex between the candidate peptide and an HLA antigen is recognized by CTL, in other words, whether or not a candidate peptide has an activity as a tumor antigen peptide.

A specific example of method for identifying tumor antigen peptides of the present invention is a method described in *J. Immunol.*, 154:2257, 1995. Specifically, peripheral blood lymphocytes are isolated from a human who is positive for the type of an HLA antigen that is expected to present the candidate peptide, and are stimulated in vitro by adding the candidate peptide. If the candidate induces CTL that specifically recognizes the HLA-antigen-presenting cells pulsed with the candidate peptide, it is indicated that the particular candidate peptide may function as a tumor antigen peptide. In this connection, the presence or absence of CTL induction can be detected, for example, by measuring the amount of various cytokines (for example, IFN-γ) produced by CTLs in response to the antigen peptide-presenting cells using, for example, an ELISA method. Alternatively, a method in which the cytotoxicity of CTLs against antigen peptide-presenting cells labeled with $^{51}$Cr is measured ($^{51}$Cr release assay, *Int. J. Cancer,* 58:317, 1994) may also be used for such detection.

Furthermore, the above detection can also be achieved as follows. An expression plasmid expressing a cDNA for the type of an HLA antigen that is expected to present the candidate peptide is incorporated into, for example, COS-7 cells (ATCC No. CRL1651) or VA-13 cells (RIKEN CELL BANK, The Institute of Physical and Chemical Research), and the resultant cells are pulsed with the candidate peptide. The cells are then reacted with the CTLs that are restricted to the type of the HLA antigen expected to present the candidate peptide as described above, and the amount of various cytokines (for example, IFN-γ) produced by said CTLs is measured (*J. Exp. Med.,* 187:277, 1998).

SART-3 contains HLA-A24- or HLA-A2-restricted tumor antigen peptide portions. In order to identify HLA-A24-restricted tumor antigen peptides, HLA-A24 cDNA (*Cancer Res.,* 55:4248-4252, 1995, Genbank Accession No. M64740) can be used as a cDNA encoding the HLA antigen, whereas those CTLs such as KE-4CTL (FERM BP-5954) as well as CTLs that are prepared by peptide-stimulation of human peripheral blood lymphocytes can be used as the CTLs described above. Likewise, for HLA-A2-restricted tumor antigen peptides, identification of such tumor antigen peptides can be achieved using HLA-A2 cDNA (Genbank Accession No. M84379), and using as the CTLs described above those CTLs such as OK-CTL (FERM BP-6818) as well as CTLs that are prepared by peptide-stimulation of human peripheral blood lymphocytes.

Specific examples of various assays as described above are illustrated in Examples 4, 6, and 8 hereinafter.

In cases like HLA-A26 wherein a relevant peptide motif is not elucidated, tumor antigen peptides of the present invention can be identified, for example, according to the method described in WO 97/46676, which method is different from that in the above cases wherein the sequence rules (motifs) have been elucidated, provided that a CTL line recognizing a complex between HLA-A26 and a tumor antigen peptide is available.

The methods for identifying tumor antigen peptides as described above may be hereinafter collectively referred to as "assay methods for tumor antigen peptides".

As described above, it is known that the sequences of tumor antigen peptides that are bound to and presented on HLA-A24 obey a certain rule (motif), and in particular, the motif is that, in a sequence of a peptide consisting of 8 to 11 amino acids, the amino acid at position 2 is tyrosine, phenylalanine, methionine, or tryptophan, and the amino acid at the C-terminus is phenylalanine, leucine, isoleucine, tryptophan, or methionine (*J. Immunol.,* 152:3913, 1994; *Immunogenetics,* 41: p 178, 1995; *J. Immunol.,* 155: p 4307, 1994). Likewise, a similar rule (motif) can be found in the sequences of tumor antigen peptides that are bound to and presented on HLA-A2, and in particular, the motifs shown in the above Table 1 are known (*Immunogenetics,* 41, p 178, 1995; *J. Immunol.,* 155: p 4749, 1995). As shown above, sequences expected to be capable of binding to HLA antigens may be further searched on the Internet using the BIMAS software of NIH.

Accordingly, HLA-A24- and HLA-A2-restricted tumor antigen peptides among the tumor antigen peptides of the present invention are exemplified by those tumor antigen peptides that are partial peptides involved in such motif structures or structures expected to be capable of binding to the HLAs in the amino acid sequence of SART-3 shown in SEQ ID NO: 2 and that are capable of binding to respective HLA antigens and being recognized by CTLs.

Particular examples of HLA-A24-restricted tumor antigen peptides described above include those tumor antigen peptides that comprise all or part of an amino acid sequence shown in any one of SEQ ID NOs: 3-24 and that are capable of binding to an HLA-A24 antigen and being recognized by CTL. Likewise, particular examples of HLA-A2-restricted tumor antigen peptides include those tumor antigen peptides that comprise all or part of an amino acid sequence shown in any one of SEQ ID NOs: 25-52 and that are capable of binding to an HLA-A2 antigen and being recognized by CTL.

Specifically, examples of tumor antigen peptides of the present invention include:
1) peptides that consist of an amino acid sequence shown in any one of SEQ ID NOs: 3-52, and
2) peptides that comprise the full length or a consecutive portion of an amino acid sequence shown in any one of SEQ ID NOs: 3-52 and that are elongated in the N-terminal and/or C-terminal direction as compared to said amino acid sequence, or peptides consisting of a consecutive portion of an amino acid sequence shown in any one of SEQ ID NOs: 3-52, said peptides being capable of binding to respective HLA antigens and being recognized by CTLs. The peptides in the above 2) may be about 8-11 amino acids in length in view of the fact that they are bound and presented by respective HLA antigens.

Suitable examples of HLA-A24-restricted tumor antigen peptides of the present invention include those tumor antigen peptides that comprise all or part of the amino acid sequence shown in any one of SEQ ID NOs: 3-9 and that are capable of binding to an HLA-A24 antigen and being recognized by CTL. Specifically, examples are:
1) peptides that consist of the amino acid sequence shown in any one of SEQ ID NOs: 3-9, and
2) peptides that comprise the full length or a consecutive portion of the amino acid sequence shown in any one of SEQ ID NOs: 3-9 and that are elongated in the N-terminal and/or C-terminal direction as compared to said amino acid sequence, or peptides that consist of a consecutive portion of the amino acid sequence shown in any one of SEQ ID NOs: 3-9, said peptides being capable of binding to HLA-A24 antigens and being recognized by CTLs. The peptides in the above 2) may be about 8-11 amino acids in length in view of the fact that they are bound to and presented on HLA-A24 antigens.

Suitable examples of HLA-A2-restricted tumor antigen peptides of the present invention include those tumor antigen peptides that comprise all or part of the amino acid sequence shown in any one of SEQ ID NOs: 25-29 and that are capable of binding to an HLA-A2 antigen and being recognized by CTL. Specifically, examples are:
1) peptides that consist of the amino acid sequence shown in any one of SEQ ID NOs: 25-29, and
2) peptides that comprise the full length or a consecutive portion of the amino acid sequence shown in any one of SEQ ID NOs: 25-29 and that are elongated in the N-terminal and/or C-terminal direction as compared to said amino acid sequence, or peptides that consist of a consecutive portion of the amino acid sequence shown in any one of SEQ ID NOs: 25-29, said peptides being capable of binding to HLA-A2 antigens and being recognized by CTLs. The peptides in the above 2) may be about 8-11 amino acids in length in view of the fact that they are bound to and presented on HLA-A2 antigens.

In the present invention, the term "derivative having properties functionally equivalent to those of a tumor antigen peptide" (hereinafter may be simply referred to as tumor antigen peptide derivative) refers to an altered peptide, of which the amino acid sequence contains alteration of one or more, preferably one to several, amino acid residues of an amino acid sequence of a tumor antigen peptide of the present invention, and which has the properties as a tumor antigen peptide, that are to be capable of binding to an HLA antigen and being recognized by CTL. Accordingly, all altered peptides fall within the scope of tumor antigen peptide of the present invention so long as they contains alteration of one or more amino acid residues of an amino acid sequence of a tumor antigen peptide of the present invention, and have the properties as tumor antigen peptides, that is, are capable of binding to HLA antigens and being recognized by CTLs.

In this context, "alteration" of an amino acid residue means substitution, deletion and/or addition (including addition of amino acids to the N-terminus and/or the C-terminus of the peptide) of an amino acid residue, with substitution of an amino acid residue being preferred. For alterations involving substitution of an amino acid residue, although the number and the position of amino acid residues to be substituted may be determined arbitrarily so long as the activity as a tumor antigen peptide is retained, it is preferred that one to several residues are substituted in light of the fact that tumor antigen peptides are usually about 8 to 14 amino acids in length as described above.

A preferred length of tumor antigen peptide derivatives of the present invention is about 8 to 14 amino acids as in case of the tumor antigen peptide described above, although derivatives of 14 or more amino acids long may also be possible for HLA-DR, -DP, and -DQ.

Such tumor antigen peptide derivatives of the present invention may be identified by synthesizing altered peptides that contain alteration of a part of a tumor antigen peptide of the present invention in accordance with the above preparation of peptide, and by conducting the above assay for tumor antigen peptides.

As described above, the sequence rules (motifs) for peptides that are bound to and presented on HLA types such as HLA-A1, -A0201, -A0204, -A0205, -A0206, -A0207, -A11, -A24, -A31, -A6801, -B7, -B8, -B2705, -B37, -Cw0401, and -Cw0602 have been elucidated. As shown above, peptide sequences expected to be capable of binding to HLA antigens may be further searched on internet using the internet using the BIMAS software of NIH. Consequently, tumor antigen peptide derivatives containing the alteration of the amino acids in a tumor antigen peptide of the present invention can be prepared on the basis of such motifs.

For example, regarding the motif for antigen peptides that are bound to and presented on HLA-A24, it is known as described above that in the sequence of a peptide consisting of 8 to 11 amino acids, the amino acid at position 2 is tyrosine, phenylalanine, methionine, or tryptophan, and the amino acid at the C-terminus is phenylalanine, leucine, isoleucine, tryptophan, or methionine (J. Immunol., 152:3913, 1994; Immunogenetics, 41:178, 1995; J. Immunol., 155:4307, 1994). Likewise, the motifs shown in the above Table 1 are known for HLA-A2. In addition, peptide sequences expected to be capable of binding to HLA antigens are laid open on the internet (BIMAS software from NIH), and amino acid residues having properties similar to those of amino acids according to the motifs may also be possible. Accordingly, examples of tumor antigen peptide derivatives of the present invention include those peptide derivatives that comprise all or part of an amino acid sequence of the tumor antigen peptide of the present invention in which one or more amino acid residues at any positions that may be allowed for substitution according to the motifs (for HLA-A24 and HLA-A2, position 2 and the C-terminus) are substituted by other amino acids (preferably, which is the amino acid expected to be capable of binding to the antigens according to the above internet), and which derivatives have activity of binding to HLA antigens and being recognized by CTLs. Preferred examples are those tumor antigen peptide derivatives that comprise all or part of an amino acid sequence in which amino acid residues to be substituted are selected from those at said positions according to the above motifs, and which derivatives have the above activity. A preferred length of "all or part" of an amino acid sequence is about 8 to 14 amino acids, although it may be a length of 14 or more amino acids for HLA-DR, -DP, and -DQ.

Examples of HLA-A24- or HLA-A2-restricted tumor antigen peptide derivatives include those peptide derivatives that comprise all or part of an amino acid sequence in which one or more amino acid residues at positions that are allowed for substitution according to the above motifs, specifically, at position 2 and/or the C-terminus, of a peptide derived from the amino acid sequence of SART-3 having a binding motif for HLA-A24 or HLA-A2 are substituted by other amino acid residues (preferably, which is the amino acid expected to be capable of binding to the antigens according to the above internet), and which derivatives have the above activity. Preferred examples are those tumor antigen peptide derivatives that comprise all or part of an amino acid sequence in which the amino acid residues at position 2 and/or the C-terminus are substituted by the amino acid residues involved according to the above motifs, and which derivatives have the above activity. In such HLA-A24- or HLA-A2-restricted tumor antigen peptide derivatives, a preferred length of "all or part" of the amino acid sequence is about 8 to 11 amino acids.

In particular, examples are those tumor antigen peptide derivatives that comprise all or part of an amino acid sequence in which the amino acid residues at position 2 and/or the C-terminus of an amino acid sequence shown in any one of SEQ ID NOs: 3 to 52 are substituted by other amino acid residues (preferably, which is the amino acid expected to be capable of binding to the antigens according to internet as shown above) and which derivatives have the above activity. Preferred examples are those tumor antigen peptide derivatives that comprise all or part of an amino acid sequence in which the amino acid residues at position 2 and/or the C-terminus of an amino acid sequence shown in any one of SEQ ID NOs: 3 to 52 are substituted by the amino acid residues involved according to the above motifs and which derivatives have the above activity. Specifically, examples of HLA-A24-restricted tumor antigen derivatives are those tumor antigen peptide derivatives that comprise all or part of an amino acid sequence in which the amino acid residue at position 2 of an amino acid sequence shown in any one of SEQ ID NOs: 3 to 24 is substituted by tyrosine, phenylalanine, methionine, or tryptophan and/or the amino acid residue at the C-terminus is substituted by phenylalanine, leucine, isoleucine, tryptophan, or methionine and which derivatives have the above activity. Likewise, examples of HLA-A2-restricted tumor antigen derivatives are those tumor antigen peptide derivatives that comprise all or part of an amino acid sequence in which the amino acid residue at position 2 of an amino acid sequence shown in any one of SEQ ID NOs: 25 to 52 is substituted by leucine, methionine, valine, isoleucine, or glutamine, and/or the amino acid residue at the C-terminus is substituted by valine or leucine and which derivatives have the above activity.

Suitable examples of HLA-A24-restricted tumor antigen peptide derivatives of the present invention are those tumor antigen peptide derivatives that comprise all or part of an amino acid sequence in which the amino acid residues at position 2 and/or the C-terminus of the amino acid sequence shown in any one of SEQ ID NOs: 3 to 9 are substituted by other amino acid residues and which derivatives have the above activity. More preferred examples are those tumor antigen peptide derivatives comprise all or part of an amino acid sequence in which the amino acid residue at position 2 of an amino acid sequence shown in any one of SEQ ID NOs: 3 to 9 is substituted by tyrosine, phenylalanine, methionine, or tryptophan and/or the amino acid residue at the C-terminus is substituted by phenylalanine, leucine, isoleucine, tryptophan, or methionine and which derivatives have the above activity. Suitable examples of such tumor antigen peptide derivatives are shown in SEQ ID NOs: 53 to 59.

Suitable examples of HLA-A2-restricted tumor antigen peptide derivatives of the present invention are those tumor antigen peptide derivatives that comprise all or part of an amino acid sequence in which the amino acid residues at position 2 and/or the C-terminus of the amino acid sequence shown in any one of SEQ ID NOs: 25 to 29 are substituted by other amino acid residues and which derivatives have the above activity. More preferred examples are those tumor antigen peptide derivatives comprise all or part of an amino acid sequence in which the amino acid residue at position 2 of an amino acid sequence shown in any one of SEQ ID NOs: 25 to 29 is substituted by leucine, methionine, valine, isoleucine, or glutamine, and/or the amino acid residue at the C-terminus is substituted by valine or leucine, and which derivatives have the above activity. Suitable examples of such tumor antigen peptide derivatives are shown in SEQ ID NOs: 60 to 64.

A tumor antigen peptide or its derivative of the present invention can be used solely or together with other one or more of them as a pharmaceutical composition for treating or preventing tumors. Namely, the present invention provides a pharmaceutical composition for treatment or prevention for tumors, which comprises the tumor antigen peptides or derivatives thereof as an active ingredient. When the composition for treating or preventing tumors which comprises as an active ingredient a tumor antigen peptide or its derivative of the present invention is administered to a SART-3-positive patient, the tumor antigen peptide or derivative thereof is presented with an HLA antigen of antigen-presenting cells, and therefore, CTLs specific for the presented HLA antigen complex proliferates and destroys the tumor cells. As a result, the tumor of the patient may be treated, or proliferation or metastasis of the tumor may be prevented. SART-3 is developed extensively on the squamous cell carcinoma such as esophageal cancer, and therefore, the composition for treating or preventing tumors according to the present invention is advantageous in terms of wide applicability. The squamous cell carcinoma often exhibits a resistance to chemotherapy and radiotherapy, and, therefore, the composition for treating tumors of the present invention also can achieve an increased therapeutic effect by its combined use.

The composition for treating or preventing tumors comprising as an active ingredient a tumor antigen peptide or its derivative of the present invention may be administered together with an adjuvant in order to effectively establish the cellular immunity, or may be administered in a particulate dosage form. For such purpose, those adjuvants described in the literature (*Clin. Microbiol. Rev.*, 7:277-289, 1994) are applicable. In addition, liposomal preparations, particulate preparations in which the ingredient is bound to beads having a diameter of several µm, or preparations in which the ingredient is attached to lipids are also possible. Administration may be achieved, for example, intradermally, hypodermically, or by intravenous injection. Although the amount of a tumor antigen peptide or its derivative of the present invention in the formulation to be administered may be adjusted as appropriate depending on, for example, the disease to be treated, the age and the body weight of the particular patient, it is typical to administer 0.0001 mg to 1000 mg, preferably 0.001 mg to 100 mg, and more preferably 0.01 mg to 10 mg every several days to every several months.

Furthermore, a recombinant DNA that contains at least one DNA encoding a tumor antigen peptide or its derivative of the present invention, or a recombinant polypeptide obtainable by expression of said recombinant DNA may be also comprised as an active ingredient in the composition for treating or preventing tumors according to the present invention, which details are provided below.

In this connection, the term "recombinant DNA" refers to any DNA encoding a partial polypeptide, a partial peptide consisting of a part of the tumor antigen protein of the present invention, derivatives thereof, polytope in which such peptides are combined, or the like. All DNAs fall within the scope of recombinant DNA of the present invention so long as they contain at least one DNA encoding the tumor antigen peptide or its derivative of the present invention. Such recombinant DNA may be incorporated into a suitable expression vector to make an active ingredient comprised in the pharmaceutical composition for treating or preventing tumors.

The term "polytope" refers to a combined peptide of many CTL epitopes, and DNAs encoding such polytopes have recently been used for DNA vaccination. See, for example, *J. of Immunology*, 160, p 1717, 1998. DNA encoding the polytope of the present invention can be prepared by ligating one or more DNAs encoding the tumor antigen peptide or its derivative of the present invention each other, and, if desired, ligating a DNA encoding other tumor antigen peptide(s).

Recombinant DNA of the present invention can be easily prepared according to typical DNA synthesis and genetic engineering method, for example, according to the description of a standard text such as "Molecular Cloning", 2nd ed., Cold Spring Harbor Laboratory Press (1989). Incorporation of such recombinant DNA into expression vectors may be also conducted according to the standard text and the like.

Determination whether or not a recombinant DNA of the present invention as prepared above may generate tumor antigen peptides that are capable of binding to HLA antigens and being recognized by CTLs may be achieved in accordance with, for example, the method as mentioned above for determining the activity of DNA of the present invention. Likewise, a method for using the present recombinant DNA as medicaments or prophylactics may be in accordance with the method for the DNA of the present invention.

As shown above, "recombinant polypeptide" obtainable by expression of the recombinant DNA of the invention may also be used for a pharmaceutical composition for treating or preventing tumors.

The recombinant polypeptide of the invention may be prepared in a similar manner to that for the protein of the invention as described above. Likewise, determination whether or not a recombinant polypeptide of the present invention as prepared above may have certain activity may be achieved in accordance with a similar manner to that for the protein of the present invention. Further, a method for using the present recombinant polypeptide as medicaments or prophylactics may be in accordance with the above method for the protein or peptide of the present invention.

The present invention also provides antibodies that specifically bind to a protein of the present invention, a tumor antigen peptide of the present invention or a derivative thereof. Such antibodies are easily prepared, for example, according to a method described in "Antibodies: A Laboratory Manual", Lane, H. D. et al. eds., Cold Spring Harbor Laboratory Press, New York, 1989. Specifically, antibodies that recognize a tumor antigen peptide or its derivative of the present invention and antibodies that further neutralize its activity may easily be prepared using the tumor antigen peptide or derivative thereof to appropriately immunize an animal in the usual manner. Such antibodies may be used in affinity chromatography, immunological diagnosis, and the like. Immunological diagnosis may be selected as appropriate from immunoblotting, radioimmunoassay (RIA), enzyme-linked immunosorbent assay (ELISA), a fluorescent or luminescent assay, and the like.

A tumor antigen peptide, derivative thereof, tumor antigen protein, gene therefor of the present invention, or a recombinant DNA or recombinant polypeptide of the present invention may also be used in vitro for treatment of tumor patients as follows.

On usage of a tumor antigen peptide, derivative thereof, tumor antigen protein, or gene therefor in treatment of tumors, it is important to establish an administration method which can efficiently induce specific CTLs in the body of a patient. As one of the means therefor, the present invention provides an antigen-presenting cell in which a complex between an HLA antigen and a tumor antigen peptide or its derivative of the present invention is presented on the surface of a cell having antigen-presenting ability isolated from a tumor patient, and also provides a pharmaceutical composition for treating tumors, which comprises said antigen-presenting cell as an active ingredient.

In this context, the "cell having antigen-presenting ability" is not limited to a specific cell so long as it is a cell expressing on its cell surface an HLA antigen allowing a tumor antigen peptide or its derivative of the present invention to be presented, and dendritic cells, which is reported to have especially a high antigen-presenting ability, are preferred.

Substances to be added to prepare an antigen-presenting cell of the present invention from the above-mentioned cell having an antigen-presenting ability may be tumor antigen peptides or their derivatives of the present invention, as well as DNAs, proteins, recombinant DNAs or recombinant polypeptides of the present invention. When used in the form of a protein or DNA, it is necessarily introduced into cells.

In order to prepare antigen-presenting cells of the present invention, cells having an antigen-presenting ability are isolated from a tumor patient, and pulsed ex vivo with a tumor antigen peptide, a derivative thereof, a tumor antigen protein, or recombinant polypeptide of the present invention to present a complex between an HLA antigen and said tumor antigen peptide or derivative thereof (*Cancer Immunol. Immunother.*, 46:82, 1998; *J. Immunol.* 158: p 1796, 1997; *Cancer Res.*, 59:1184, 1999). When dendritic cells are used, antigen-presenting cells of the present invention may be prepared, for example, by isolating lymphocytes from peripheral blood of a tumor patient using Ficoll method, removing non-adherent cells, incubating the adherent cells in the presence of GM-CSF and IL-4 to induce dendritic cells, and incubating and pulsing said dendritic cells with a tumor antigen peptide or tumor antigen protein of the present invention, or the like.

When antigen-presenting cells of the present invention are prepared by introducing a DNA or a recombinant DNA of the present invention into the aforementioned cells having an antigen-presenting ability, said gene may be in the form of DNA or RNA. In particular, DNA may be used consulting, for example, *Cancer Res.*, 56:5672, 1996 or *J. Immunol.*, 161: p 5607, 1998, and RNA may be used by consulting, for example, *J. Exp. Med.*, 184: p 465, 1996.

A pharmaceutical composition for treating tumors which comprises the above antigen-presenting cells as an active ingredient preferably contains physiological saline, phosphate buffered saline (PBS), medium, or the like to stably maintain the antigen-presenting cells. It may be administered, for example, intravenously, subcutaneously, or intradermally. By reintroducing such composition for treating tumors which comprises antigen-presenting cells as an active ingredient into the body of the patient, specific CTLs are efficiently induced in SART-3-positive patient so as to achieve treatment of the tumor. It should be undisputed that the HLA types need be compatible between the patient and the peptide used, such that an HLA-A24-restricted tumor antigen peptide or a derivative thereof must be used with an HLA-A24-positive tumor patient.

In addition, in vitro use of a tumor antigen peptide, a derivative thereof, a tumor antigen protein, a DNA therefor a recombinant DNA or recombinant polypeptide according to the present invention in the following adoptive immuno-therapy may be provided as another example of their use.

For melanomas, it has been observed that an adoptive immunotherapy wherein tumor-infiltrating T cells taken from the patient himself/herself are cultured ex vivo in large quantities, and then returned into the patient, achieves a therapeutic effect (*J. Natl. Cancer. Inst.*, 86:1159, 1994). Likewise, in mouse melanoma, suppression of metastasis has been observed by in vitro stimulation of splenocytes with tumor antigen peptide TRP-2, thereby proliferating CTLs specific for the tumor antigen peptide, and administering said CTLs into a melanoma-grafted mouse (*J. Exp. Med.*, 185:453, 1997). This resulted from in vitro proliferation of CTLs that specifically recognize the complex between an HLA antigen of antigen-presenting cells and the tumor antigen peptide. Accordingly, a method for treating tumors is believed to be useful, which comprises stimulating in vitro peripheral blood lymphocytes from a patient using a tumor antigen peptide, a derivative thereof, a tumor antigen protein, or a DNA therefor according to the present invention to proliferate tumor-specific CTLs, and subsequently returning the CTLs into the patient.

Thus, the present invention provides CTLs that specifically recognize a complex between the HLA antigen and the tumor antigen peptide or derivative thereof, and also provides a pharmaceutical composition for treating tumors which comprises said CTLs as an active ingredient. Such composition preferably contains physiological saline, phosphate buffered saline (PBS), medium, or the like to stably maintain CTLs. It may be administered, for example, intravenously, subcutaneously, or intradermally. By reintroducing the composition for treating tumors which comprises CTLs as an active ingredient into the body of the patient, the toxic effect of CTLs against the tumor cells is enhanced in SART-3-positive patient and thereby destroys the tumor cells to achieve treatment of the tumor.

Tumor antigen peptides, derivatives thereof, tumor antigen proteins, or recombinant polypeptide thereof according to the present invention may be also used as an active ingredient of a diagnostic agent for diagnosing tumors. Specifically, by using a tumor antigen peptide, or derivative thereof according to the present invention itself as a diagnostic agent to detect the presence of antibodies in a sample (such as blood or a tumor tissue) obtained from a patient suspected to have a tumor, early detection of tumors and diagnosis of recurrence and metastasis are possible. The same procedure can also be used for selection of tumor patients to whom medicaments comprising as an active ingredient, for example, a tumor antigen peptide of the present invention can be applied. In particular, such diagnosis may be conducted using immunoblotting, RIA, ELISA, or a fluorescent or luminescent assay.

Furthermore, in recent years, a new detection method has been established for detecting antigen-specific CTLs using a complex between the antigen peptide and an HLA antigen (Science, 274:94, 1996). Early detection of tumors and diagnosis of reoccurrence or metastasis are possible by applying a complex between a tumor antigen peptide or derivative thereof according to the present invention and an HLA antigen to the above detection method, and thereby detecting tumor antigen-specific CTLs. The same procedure can also be used for selection of tumor patients to whom a medicine comprising as an active ingredient, for example, a tumor antigen peptide of the present invention can be applied, or for determination of the therapeutic effect of said medicament. Thus, the present invention also provides a diagnostic agent for tumors comprising a tumor antigen peptide or derivative thereof according to the present invention.

In particular, such diagnosis may be conducted by preparing a tetramer of a complex between an HLA antigen fluorescently labeled according to the method described in the literature (Science, 274:94, 1996) and a tumor antigen peptide, and using it to quantitatively determine the antigen peptide-specific CTLs in peripheral blood lymphocytes of a patient suspected to have a tumor using a flow cytometer.

The present invention also provides OK-CTL (deposit number FERM BP-6818) that is CTL established from tumor-infiltrating lymphocytes derived from colon cancer, OK-CTL has proved to be HLA-A2-restricted. Accordingly, tumor antigen proteins and HLA-A2-restricted tumor antigen peptides may be newly found by using OK-CTL. For details, see Example 8 below.

BEST MODE FOR CARRYING OUT THE INVENTION

The present invention is further illustrated by the following examples, but is not limited by these examples in any respect.

Reference 1
Establishment of Cytotoxic T Lymphocyte (CTL) Cell Line Against Esophageal Cancer Cell Line According to the description of Nakao et al., Cancer Res., 55:4248-4252 (1995), CTL against esophageal cancer cell line KE-4, which belongs to squamous cell carcinomas when classified on the basis of tissue type, was established from peripheral blood mononuclear cells of a patient, named KE-4CTL, and used in the following experiments. Esophageal cancer cell lines KE-4 and KE-4CTL have been deposited at The National Institute of Bioscience and Human Technology (1-1-3 Higashi, Tsukuba, Ibaraki, Japan) under International Deposition Nos. FERM BP-5955 and FERM BP-5954, respectively, both on May 23, 1997. Further, typing of HLA class I molecules of KE-4 was conducted according to the above-mentioned description of Nakao et al., to find that they are HLA-A2402, -A2601, -B54, -B60, -Cw1, and -Cw3.

Reference 2
Preparation of HLA-A2402 cDNA

According to the description of Nakao et al., Cancer Res., 55: 4248-4252 (1995), a recombinant plasmid was prepared from KE-4 by incorporating cDNA for HLA-A2402 (Genbank Accession No. M64740) into an expression vector pCR3 (INVITROGEN).

Reference 3
Preparation of cDNA Library Derived from KE-4

Poly (A)$^+$ mRNA was prepared from KE-4 by isolation of total RNA fraction and purification on oligo (dT) column using mRNA Purification system (Pharmacia Biotech) according to the manufacturer's protocol. cDNAs having Not I adapter and Sca I adapter linked to each terminus were prepared from the mRNAs using SuperScript Plasmid System (GIBCO BRL) according to the manufacturer's protocol, and then ligated into the restriction sites Not I and Sal I of an expression vector, plasmid pSV-SPORT1 (GIBCO BRL), to yield recombinant plasmids. The recombinant plasmids were introduced into E. coli. ElectroMAX DH10B™ cells (GIBCO BRL) using electric pulses in Gene Pulser (Bio-Rad) under a condition of 25 μF and 2.5 kV. Transformants into which the recombinant plasmids had been introduced were selected in LB medium (1% bacto-trypton, 0.5% yeast extract, 0.5% NaCl, pH7.3) containing ampicillin (50 μg/ml).

Example 1

Screening of Novel Tumor Antigen Protein Gene

The recombinant plasmid DNAs were recovered as follows, from pools of about 100 transformants described in Reference 3. A hundred transformants were introduced and cultured in each well of 96-well U-bottomed microplate containing LB medium plus ampicillin (50 μg/ml). Part of the culture was then transferred to another 96-well U-bottomed microplate containing 0.25 ml of TYGPN medium per well (F. M. Ausubel et al., Current Protocols in Molecular Biology, John Wiley & Sons, Inc.), and cultured at 37° C. for 48 hours. The remaining cultures in LB medium on the microplate were stored in frozen. Preparation of recombinant plasmid DNAs from transformants cultured in TYGPN medium was achieved in the microplate by the alkaline lysis method (F. M. Ausubel et al., Current Protocols in Molecular Biology, John Wiley & Sons, Inc.). The recombinant plasmid DNAs recovered by isopropanol precipitation were suspended in 50 μl of 10 mM Tris, 1 mM EDTA, pH 7.4, containing 20 ng/ml RNase.

The recombinant plasmid for KE-4 cDNA and the recombinant plasmid for HLA-A2402 cDNA were doubly transfected into fibroblast cell line VA-13 cells (RIKEN CELL BANK, The Institute of Physical and Chemical Research; Ann. Med. Exp. Biol. Fenn., 44:242-254, 1966) using the Lipofectin method as follows. Seven thousands VA-13 cells were placed into each well of 96-well flat-bottomed microplate, and incubated for 2 days in 100 μl of RPMI 1640 medium containing 10% FCS. Using Lipofectin reagent (GIBCO BRL), a 30 μl portion of mixture 70 μl consisting of 25 μl of the recombinant plasmid for KE-4 cDNA corresponding to about 100 transformants, 10 μl (200 ng) of the recombinant plasmid for HLA-A2402 cDNA described in Reference 2, and 35 μl of about 35-fold diluted Lipofectin reagent was added to VA-13 cells, and allowed to doubly transfect them. Transfectants were prepared in duplicate. After 5 hours, the transfectants was added with 200 μl of culture medium containing 10% FCS, and further incubated at 37° C. for 72 hours. After removing the culture medium, 10,000 KE-4CTL cells were added to each well, and cultured at 37° C. for 24 hours in 100 μl of culture medium containing 10% FCS and 25 U/ml IL-2. The culture medium was recovered, and the amount of IFN-γ in the culture was measured by ELISA as described below.

Specifically, an anti-human IFN-γ mouse monoclonal antibody was adsorbed on wells of 96-well microplate as a solid-phased antibody, and after blocking non-specific bindings with bovine serum albumin, the antibody was allowed to bind to IFN-γ in the above-described sample. Anti-human IFN-γ rabbit polyclonal antibody as a detection antibody was then allowed to bind, and after binding to an anti-rabbit immunoglobulin goat antibody labeled with alkaline phosphatase, para-nitrophenyl phosphate was reacted as a chromogenic substrate. After quenching the reaction by adding an equal volume of 1N NaOH, absorbance at 405 nm was measured. The absorbance was compared with that obtained with standard IFN-γ to determine the amount of IFN-γ in the sample.

Regarding the groups in which high production of IFN-γ was observed, the corresponding frozen-stored pools of about 100 transformants containing recombinant plasmids for KE-4 cDNA were used in the following screening. The pools of the transformants were plated on LB agar medium containing ampicillin (50 µg/ml) to obtain colonies. Two hundreds colonies for each group were cultured as described above so that a single kind of transformant is included in each well, thereby preparing recombinant plasmid DNAs for KE-4 cDNA. Then, VA-13 cells were doubly transfected with the recombinant plasmid for KE-4 cDNA and the recombinant plasmid for HLA-A2402 cDNA, followed by co-cultivation with KE-4CTL, and IFN-γ produced due to KE-4CTL reaction was quantitatively determined as described above so as to select positive plasmids. In this manner, a single KE-4 cDNA recombinant plasmid clone was selected and named clone 13. Additional analysis revealed that clone 13 was incorporated with about 1.2 kb cDNA. Furthermore, similar procedures were repeated with clone 13 to determine the amount of IFN-γ produced by KE-4CTL according to a similar method to that described above. The results are shown in Table 2.

TABLE 2

| Target cell | Amount of IFN-γ produced by KE-4CTL (pg/ml) |
| --- | --- |
| VA-13 + HLA-A2402 | 326 |
| VA-13 + HLA-A2402 + clone 13 | 775 |

When compared to VA-13 transfected with only HLA-A2402, KE-4CTL reacted more strongly to VA-13 doubly transfected with HLA-A2402 and clone 13, and produced more IFN-γ. This result indicated that the protein encoded by clone 13 is a tumor antigen protein.

Example 2

Cloning of Full-Length cDNA Clone Encoding Tumor Antigen Protein

In order to determine the length of the full-length cDNA gene incorporated in clone 13 obtained in Example 1, Northern Hybridization was conducted as described blow.

First of all, RNAs were prepared from esophageal cancer cell line KE-4 using RNAzol B (TEL-TEST, Inc.). Five µg of RNA was denatured in the presence of formamide and formaldehyde, electrophoresed on agarose, and then transferred and fixed onto Hybond-N+ Nylon membrane (Amersham). The inserted sequence region of clone 13 was labeled with $^{32}$P using Multiprime DNA labeling system (Amersham) to prepare a DNA probe. According to the known method (Nakayama et al., *Bio-Jikken-Illustrated*, vol. 2, "Idenshi-Kaiseki-No-Kiso (A Basis for Gene Analysis)", pp. 148-151, Shujunsha, 1995), this probe was allowed to hybridize to RNAs on the membranes, and subjected to autoradiography to detect mRNA for cDNA incorporated in clone 13, indicating that the mRNA was about 3.8 kb in full length. Then, the full-length cDNA clone containing clone 13 as prepared above was cloned. KE-4-derived cDNA Library described in Reference 3 was plated on LB agar medium containing ampicillin (50 µg/ml) to obtain colonies. The colonies were then transferred to and fixed on Hybond-N+ nylon membrane (Amersham) according to the manufacturer's protocol. DNA probe in which the insertion sequence of clone 13 was labeled with $^{32}$P was employed for hybridization and autoradiography under similar conditions to those mentioned above in order to select colonies representing positive transformants. Recombinant plasmids were then recovered from the many colonies selected, treated with restriction enzymes Not I and Sal I, and then electrophoresed on agarose to determine the length of incorporated cDNAs. A recombinant plasmid incorporating cDNA of about 3.8 kb was selected, and named clone K. VA-13 Cells were then doubly transfected with the recombinant plasmid clone K incorporating cDNA for the tumor antigen protein gene and another recombinant plasmid containing cDNA for HLA-A2402 as described above, and the cells were used as target cells. The amount of IFN-γ produced by the reaction of KE-4CTL was determined according to the method as described above. The results are shown in Table 3.

TABLE 3

| Target cell | Amount of IFN-γ produced by KE-4CTL (pg/ml) |
| --- | --- |
| VA-13 + HLA-A2403 | 342 |
| VA-13 + HLA-A2402 + clone K | 627 |

When compared to VA-13 transfected with only HLA-A2402, KE-4CTL reacted more strongly to VA-13 doubly transfected with HLA-A2402 and clone K, and produced more IFN-γ. This result indicated that the protein encoded by clone K is a tumor antigen protein. The tumor antigen protein encoded by clone K is named SART-3 (squamous cell carcinoma antigens recognized by T cells-3).

Example 3

Determination of Base Sequence of Tumor Antigen Protein Gene

The base sequence of the DNA of tumor antigen protein SART-3 as obtained in Example 3 was determined using DyeDeoxy Terminator Cycle Sequencing kit (Perkin-Elmer). The base sequence thus determined is shown in SEQ ID NO: 1. The full-length of the cDNA was 3798 base pairs. Amino acid sequence (963 amino acids) encoded by the base sequence of SEQ ID NO: 1 is shown in SEQ ID NO: 2. Comparison of the base sequence shown in SEQ ID NO: 1 to known sequences using GenBank data base revealed that the base sequence of tumor antigen protein SART-3 has a novel base sequence that is different from gene KIAA0156 registered at GenBank under Accession No. D63879 in terms of a single base (at position 108 of KIAA0156), which function has not been demonstrated.

Example 4

Selection of Candidate Peptides

There are certain rules (motifs) in the sequences of antigen peptides that should be bound and presented by HLA antigens. Regarding the motif for HLA-A24, it is known that in the sequence of peptides consisting of 8 to 11 amino acids, the amino acid at position 2 is tyrosine, phenylalanine, methionine, or tryptophan, and the amino acid at the C-terminus is phenylalanine, tryptophan, leucine, isoleucine, or methionine (*Immunogenetics*, 41:178, 1995; *J. Immunol.*, 152:3913, 1994; *J. Immunol.*, 155:4307, 1994). According to the motifs, peptide portions consisting of 8 to 11 peptides having the above motifs were selected from the amino acid sequence of tumor antigen protein SART-3 shown in SEQ ID NO: 2. Those examples of the selected peptides are shown in SEQ ID NOs: 3-24. These peptides were synthesized at Biologica Co, by the Fmoc method.

Then, $1.8 \times 10^4$ VA-13 cells were transfected with a recombinant plasmid of HLA-A2402 cDNA by the Lipofectin method to express HLA-A2402 according to the literature (*J. Exp. Med.*, 187:277, 1998). To these cells, various peptides having a binding motif for HLA-A24 that had precedently synthesized were each added at 10 μM over two hours in order to pulse the cells. The cells were then cultured with $2 \times 10^4$ KE-4CTLs for 18 hours, and the amount of IFN-γ produced by KE-4CTL in the culture supernatant was determined by the ELISA method. The results of this determination are shown in Table 4, which performed on seven peptides, that is, a peptide "109-118" comprising the sequence from position 109 to position 118 (SEQ ID NO: 3), a peptide "172-181" comprising the sequence from position 172 to position 181 (SEQ ID NO: 4), a peptide "284-292" comprising the sequence from position 284 to position 292 (SEQ ID NO: 5), a peptide "315-323" comprising the sequence from position 315 to position 323 (SEQ ID NO: 6), a peptide "416-425" comprising the sequence from position 416 to position 425 (SEQ ID NO: 7), a peptide "426-434" comprising the sequence from position 426 to position 434 (SEQ ID NO: 8), and a peptide "448-456" comprising the sequence from position 448 to position 456 (SEQ ID NO: 9), in the amino acid sequence of tumor antigen protein SART-3.

TABLE 4

| Peptides | IFN-γ in the supernatant (pg/ml) |
|---|---|
| "109-118" | 928 |
| "172-181" | 830 |
| "284-292" | 794 |
| "315-323" | 880 |
| "416-425" | 731 |
| "426-434" | 833 |
| "448-456" | 754 |
| None | 677 |

When compared to cells pulsed with no peptide, KE-4CTLs reacted more strongly to cells pulsed with the peptides, and produced more IFN-γ. This result indicated that the seven peptides function as tumor antigen peptides.

Example 5

Synthesis of Tumor Antigen Peptides

The seven peptides described above were synthesized by the solid phase method as shown below.
(1) Synthesis of SART-3 "109-118" Val-Tyr-Asp-Tyr-Asn-Cys-His-Val-Asp-Leu (SEQ ID NO: 3)
Fmoc-Leu-Alko Resin (0.55 mmol/g, 100-200 mesh) was used as a resin. Using 100 mg of this resin, the synthesis was started according to Schedule 1 described below to couple the following residues in order: Fmoc-Asp(OtBu)-OH, Fmoc-Val-OH, Fmoc-His(Boc)-OH, Fmoc-Cys(Trt)-OH, Fmoc-Asn-OH, Fmoc-Tyr(tBu)-OH, Fmoc-Asp(OtBu)-OH, Fmoc-Tyr(tBu)-OH, and Fmoc-Val-OH. After the coupling, the procedures were conducted up to Step 3 of Schedule 1 to obtain a peptide resin, To this peptide resin, 2 ml of Reagent K (the solution of 5% phenol, 5% thioanisole, 5% $H_2O$, and 2.5% ethanedithiol in TFA) was added and the mixture was allowed to react for 2.5 hours at room temperature. While cooling with ice, 10 ml of diethyl ether was added to the reaction, the mixture was stirred for 10 minutes, filtered, and washed with 10 ml of diethyl ether. To the filter cake, 10 ml of aqueous acetic acid was added, and the mixture was stirred for 30 minutes. The resin was then filtered, and washed with 4 ml of aqueous acetic acid. After lyophilizing the filtrate and the wash, the crude peptide obtained was dissolved in aqueous acetic acid, and injected into a reverse phase packing material, YMC-PACK ODS-A column (30φ×250 mm) that had been pre-equilibrated with 0.1% aqueous TFA. The column was washed with 0.1% aqueous TFA, and elution at a flow rate of 7 ml/min was then conducted, while increasing the concentration of acetonitrile up to 25% over 180 minutes. The eluate was monitored by A 220 nm. The fractions containing the desired product were combined together and lyophilized to obtain 31.0 mg of Val-Tyr-Asp-Tyr-Asn-Cys-His-Val-Asp-Leu (SEQ ID NO: 3).

The peptide obtained, Val-Tyr-Asp-Tyr-Asn-Cys-His-Val-Asp-Leu (SEQ ID NO: 3), had a retention time of 19.3 minutes in an analysis using a reverse phase packing material, YMC-PACK ODS-AM column (4.6φ×250 mm) eluted with a linear gradient of acetonitrile concentration from 16 to 46% containing 0.1% TFA, and the results of amino acid analysis (Cys being not detected) and mass spectrometry of the product were consistent with the theoretical values.

Amino Acid Analysis

Hydrolysis: 1% phenol/6N aqueous hydrochloric acid, 110° C., 8 hours;
Analysis method: the ninhydrin method;
* Reference amino acid; Theoretical values are indicated in parentheses:
  Asx: 2.77 (3)
  Val: 1.70 (2)
  *Leu: 1.00 (1)
  Tyr: 1.98 (2)
  His: 0.91 (1)

Mass Spectrum (FAB)

$[M+H]^+$: 1241

TABLE 5

| Steps | Schedule 1<br>Duration (min) × the<br>number of treatments |
|---|---|
| 1. (washing) DMF 1.2 ml | 1 × 2 |
| 2. (deprotection) 50% piperidine/DMF | 12 × 1 |
| 3. (washing) DMF 1.2 ml | 1 × 7 |
| 4. (coupling) each amino-protected amino acid (5 equivalents)/NMP solution 0.9 ml, DIC (5 equivalents)/NMP solution 0.3 ml | 30 × 1 |
| 5. (washing) DMF 1.2 ml | 1 × 2 |
| 6. (coupling) each amino-protected amino acid (5 equivalents)/NMP solution 0.9 ml, DIC (5 equivalents)/NMP solution 0.3 ml | 30 × 1 |
| 7. (washing) DMF 1.2 ml | 1 × 4 |

(2) Synthesis of SART-3 "172-181" Leu-Phe-Glu-Lys-Ala-Val-Lys-Asp-Tyr-Ile (SEQ ID NO: 4)
According to a similar manner to that described in above (1), using 100 mg of Fmoc-Ile-Alko Resin (0.41 mmol/g, 100-200 mesh), Fmoc-Tyr(tBu)-OH, Fmoc-Asp(OtBu)-OH, Fmoc-Lys(Boc)-OH, Fmoc-Val-OH, Fmoc-Ala-OH, Fmoc-Lys(Boc)-OH, Fmoc-Glu(OtBu)-OH, Fmoc-Phe-OH, and Fmoc-Leu-OH were coupled in order, and the product was then deprotected. The crude peptide obtained was dissolved in aqueous acetic acid and injected into a reverse phase packing material YMC-PACK ODS-A column (30φ×250 mm) that has been pre-equilibrated with 0.1% aqueous TFA. The column was washed with 0.1% aqueous TFA, and the elution at a flow rate of 7 ml/min was then conducted, while increasing the concentration of acetonitrile up to 30% over 300 minutes. The eluate was monitored by A 220 nm. The fractions containing the desired product were combined together and lyophilized to obtain 66.3 mg of Leu-Phe-Glu-Lys-Ala-Val-Lys-Asp-Tyr-Ile (SEQ ID NO: 4).

The peptide obtained, Leu-Phe-Glu-Lys-Ala-Val-Lys-Asp-Tyr-Ile (SEQ ID NO: 4), had a retention time of 23.8 minutes in an analysis using a reverse phase packing material YMC-PACK ODS-AM column (4.6φ×250 mm) eluted with a linear gradient of acetonitrile concentration from 12 to 42% containing 0.1% TFA, and the results of amino acid analysis and mass spectrometry of the product were consistent with the theoretical values.

Amino Acid Analysis

Hydrolysis; 1% phenol/6N aqueous hydrochloric acid, 110° C., 12 hours;
Analysis method: the ninhydrin method;
* Reference amino acid; Theoretical values are indicated in parentheses:
    Asx: 0.94 (1)
    Glx: 1.03 (1)
    Ala: 1.00 (1)
    Val: 0.88 (1)
    Ile: 0.92 (1)
    *Leu: 1.00 (1)
    Tyr: 0.96 (1)
    Phe: 0.97 (1)
    Lys: 1.45 (2)

Mass Spectrum (FAB)

$[M+H]^+$: 1225

(3) Synthesis of SART-3 "284-292" Asn-Tyr-Asn-Lys-Ala-Leu-Gln-Gln-Leu (SEQ ID NO: 5)

According to a similar manner to that described in above (1), using 100 mg of Fmoc-Leu-Alko Resin, Fmoc-Gln-OH, Fmoc-Gln-OH, Fmoc-Leu-OH, Fmoc-Ala-OH, Fmoc-Lys(Boc)-OH, Fmoc-Asn-OH, Fmoc-Tyr(tBu)-OH, and Fmoc-Asn-OH were coupled in order, and the product was then deprotected. The crude peptide obtained was dissolved in aqueous acetic acid and injected into a reverse phase packing material YMC-PACK ODS-A column (30φ×250 mm) that has been pre-equilibrated with 0.1% aqueous TFA. The column was washed with 0.1% aqueous TFA, and the elution at a flow rate of 7 ml/min was then conducted, while increasing the concentration of acetonitrile up to 30% over 300 minutes. The eluate was monitored by A 220 nm. The fractions containing the desired product were combined together and lyophilized to obtain 25.0 mg of Asn-Tyr-Asn-Lys-Ala-Leu-Gln-Gln-Leu (SEQ ID NO: 5).

The peptide obtained, Asn-Tyr-Asn-Lys-Ala-Leu-Gln-Gln-Leu (SEQ ID NO: 5), had a retention time of 19.0 minutes in an analysis using a reverse phase packing material YMC-PACK ODS-AM column (4.6φ×250 mm) eluted with a linear gradient of acetonitrile concentration from 12 to 42% containing 0.1% TFA, and the results of amino acid analysis and mass spectrometry of the product were consistent with the theoretical values.

Amino Acid Analysis

Hydrolysis: 1% phenol/6N aqueous hydrochloric acid, 110° C., 12 hours;
Analysis method: the ninhydrin method;
* Reference amino acid; Theoretical values are indicated in parentheses:
    Asx: 1.87 (2)
    Glx: 2.03 (2)
    Ala: 0.98 (1)
    *Leu: 2.00 (2)
    Tyr: 0.99 (1)
    Lys: 0.97 (1)

Mass Spectrum (FAB)

$[M+H]^+$: 1091

(4) Synthesis of SART-3 "315-323" Ala-Tyr-Ile-Asp-Phe-Glu-Met-Lys-Ile (SEQ ID NO: 6)

According to a similar manner to that described in above (1), using 100 mg of Fmoc-Ile-Alko Resin (0.62 mmol/g, 100-200 mesh), Fmoc-Lys(Boc)-OH, Fmoc-Met-OH, Fmoc-Glu(OtBu)-OH, Fmoc-Phe-OH, Fmoc-Asp(OtBu)-OH, Fmoc-Ile-OH, Fmoc-Tyr(tBu)-OH, and Fmoc-Ala-OH were coupled in order, and the product was then deprotected. The crude peptide obtained was dissolved in aqueous acetic acid and injected into a reverse phase packing material YMC-PACK ODS-A column (30φ×250 mm) that has been pre-equilibrated with 0.1% aqueous TFA. The column was washed with 0.1% aqueous TFA, and the elution at a flow rate of 7 ml/min was then conducted, while increasing the concentration of acetonitrile up to 40% over 180 minutes. The eluate was monitored by A 220 nm. The fractions containing the desired product were combined together and lyophilized to obtain 15.4 mg of Ala-Tyr-Ile-Asp-Phe-Glu-Met-Lys-Ile (SEQ ID NO: 6).

The peptide obtained, Ala-Tyr-Ile-Asp-Phe-Glu-Met-Lys-Ile (SEQ ID NO: 6), had a retention time of 19.6 minutes in an analysis using a reverse phase packing material YMC-PACK ODS-AM column (4.6φ×250 mm) eluted with a linear gradient of acetonitrile concentration from 21 to 51% containing 0.1% TFA, and the results of amino acid analysis (Met being not detected) and mass spectrometry of the product were consistent with the theoretical values.

Amino Acid Analysis

Hydrolysis: 1% phenol/6N aqueous hydrochloric acid, 110° C., 12 hours;
Analysis method: the ninhydrin method;
* Reference amino acid; Theoretical values are indicated in parentheses:
    Asx: 0.91 (1)
    Glx: 1.06 (1)
    Ala: 1.06 (1)
    Ile: 1.69 (2)
    Tyr: 0.81 (1)
    *Phe: 100 (1)
    Lys: 0.87 (1)

Mass Spectrum (FAB)

[M+H]⁺: 1130

(5) Synthesis of SART-3 "416-425" Asp-Tyr-Val-Glu-Ile-Trp-Gln-Ala-Tyr-Leu (SEQ ID NO: 7)

According to a similar manner to that described in above (1), using 100 mg of Fmoc-Leu-Alko Resin, Fmoc-Tyr(tBu)-OH, Fmoc-Ala-OH, Fmoc-Gln-OH, Fmoc-Trp(Boc)-OH, Fmoc-Ile-OH, Fmoc-Glu(OtBu)-OH, Fmoc-Val-OH, Fmoc-Tyr(tBu)-OH, and Fmoc-Asp(OtBu)-OH were coupled in order, and the product was then deprotected. The crude peptide obtained was dissolved in aqueous acetic acid and injected into a reverse phase packing material YMC-PACK ODS-A column (30φ×250 mm) that has been pre-equilibrated with 0.1% aqueous TFA. The column was washed with 0.1% aqueous TFA, and the elution at a flow rate of 7 ml/min was then conducted, while increasing the concentration of acetonitrile up to 35% over 180 minutes. The eluate was monitored by A 220 nm. The fractions containing the desired product were combined together and lyophilized to obtain 18.9 mg of Asp-Tyr-Val-Glu-Ile-Trp-Gln-Ala-Tyr-Leu (SEQ ID NO: 7).

The peptide obtained, Asp-Tyr-Val-Glu-Ile-Trp-Gln-Ala-Tyr-Leu (SEQ ID NO: 7), had a retention time of 20.5 minutes in an analysis using a reverse phase packing material YMC-PACK ODS-AM column (4.6φ×250 mm) eluted with a linear gradient of acetonitrile concentration from 25 to 55% containing 0.1% TFA, and the results of amino acid analysis (Trp being not detected) and mass spectrometry of the product were consistent with the theoretical values.

Amino Acid Analysis

Hydrolysis: 1% phenol/6N aqueous hydrochloric acid, 110° C., 10 hours;
Analysis method: the ninhydrin method;
* Reference amino acid; Theoretical values are indicated in parentheses:
  Asx: 1.00 (1)
  Glx: 2.09 (2)
  Ala: 1.04 (1)
  Val: 0.89 (1)
  Ile: 0.86 (1)
  *Leu: 1.00 (1)
  Tyr: 1.95 (2)

Mass Spectrum (FAB)

[M+H]⁺: 1300

(6) Synthesis of SART-3 "426-434" Asp-Tyr-Leu-Arg-Arg-Arg-Val-Asp-Phe (SEQ ID NO: 8)

According to a similar manner to that described in above (1), using 100 mg of Fmoc-Phe-Alko Resin (0.72 mmol/g, 100-200 mesh), Fmoc-Asp(OtBu)-OH, Fmoc-Val-OH, Fmoc-Arg(Pmc)-OH, Fmoc-Arg(Pmc)-OH, Fmoc-Arg(Pmc)-OH, Fmoc-Leu-OH, Fmoc-Tyr(tBu)-OH, and Fmoc-Asp(OtBu)-OH were coupled in order, and the product was then deprotected. The crude peptide obtained was dissolved in aqueous acetic acid and injected into a reverse phase packing material YMC-PACK ODS-A column (30φ×250 mm) that has been pre-equilibrated with 0.1% aqueous TFA. The column was washed with 0.1% aqueous TFA, and the elution at a flow rate of 7 ml/min was then conducted, while increasing the concentration of acetonitrile up to 25% over 240 minutes. The eluate was monitored by A 220 nm. The fractions containing the desired product were combined together and lyophilized to obtain 34.0 mg of Asp-Tyr-Leu-Arg-Arg-Arg-Val-Asp-Phe (SEQ ID NO: 8).

The peptide obtained, Asp-Tyr-Leu-Arg-Arg-Arg-Val-Asp-Phe (SEQ ID NO: 8), had a retention time of 20.1 minutes in an analysis using a reverse phase packing material YMC-PACK ODS-AM column (4.6φ×250 mm) eluted with a linear gradient of acetonitrile concentration from 12 to 42% containing 0.1% TFA, and the results of amino acid analysis and mass spectrometry of the product were consistent with the theoretical values.

Amino Acid Analysis

Hydrolysis: 1% phenol/6N aqueous hydrochloric acid, 110° C., 12 hours;
Analysis method: the ninhydrin method;
* Reference amino acid; Theoretical values are indicated in parentheses:
  Asx: 1.90 (2)
  Vat: 0.95 (1)
  *Leu: 1.00 (1)
  Tyr: 1.00 (1)
  Phe: 0.99 (1)
  Arg: 2.93 (3)

Mass Spectrum (FAB)

[M+H]⁺: 1239

(7) Synthesis of SART-3 "448-456" Ala-Phe-Thr-Arg-Ala-Leu-Glu-Tyr-Leu (SEQ ID NO: 9)

According to a similar manner to that described in above (1), using 100 mg of Fmoc-Leu-Alko Resin, Fmoc-Tyr(tBu)-OH, Fmoc-Glu(OtBu)-OH, Fmoc-Leu-OH, Fmoc-Ala-OH, Fmoc-Arg(Pmc)-OH, Fmoc-Thr(tBu)-OH, Fmoc-Phe-OH, and Fmoc-Ala-OH were coupled in order, and the product was then deprotected. The crude peptide obtained was dissolved in aqueous acetic acid and injected into a reverse phase packing material YMC-PACK ODS-A column (30φ×250 mm) that has been pre-equilibrated with 0.1% aqueous TFA. The column was washed with 0.1% aqueous TFA, and the elution at a flow rate of 7 ml/min was then conducted, while increasing the concentration of acetonitrile up to 30% over 240 minutes. The eluate was monitored by A 220 nm. The fractions containing the desired product were combined together and lyophilized to obtain 22.8 mg of Ala-Phe-Thr-Arg-Ala-Leu-Glu-Tyr-Leu (SEQ ID NO: 9).

The peptide obtained, Ala-Phe-Thr-Arg-Ala-Leu-Glu-Tyr-Leu (SEQ ID NO: 9), had a retention time of 18.1 minutes in an analysis using a reverse phase packing material YMC-PACK ODS-AM column (4.6φ×250 mm) eluted with a linear gradient of acetonitrile concentration from 20 to 50% containing 0.1% TFA, and the results of amino acid analysis and mass spectrometry of the product were consistent with the theoretical values.

Amino Acid Analysis

Hydrolysis: 1% phenol/6N aqueous hydrochloric acid, 110° C., 12 hours;
Analysis method: the ninhydrin method;
* Reference amino acid; Theoretical values are indicated in parentheses:
  Thr: 0.91 (1)
  Glx: 1.03 (1)
  Ala: 1.91 (2)
  *Leu: 2.00 (2)
  Tyr: 1.00 (1)
  Phe: 0.97 (1)
  Arg: 0.97 (1)

Mass Spectrum (FAB)

[M+H]$^+$: 1083

Example 6

CTL Induction from Peripheral Blood Lymphocytes by Tumor Antigen Peptides and Derivatives Thereof The peptides "109-118" (SEQ ID NO: 3) and "315-323" (SEQ ID NO: 6) synthesized as shown in Example 5 were investigated for their ability to induce antigen-specific CTLs from peripheral blood lymphocytes.

Using the Ficoll method, lymphocytes were separated from peripheral blood of healthy donors who were heterozygous for A24 in the HLA-A locus (referred to as HD1 and HD2, respectively). The lymphocytes were placed into wells of a 24-well plate at 2×10$^6$ cells/well, and cultured in the lymphocyte medium. The above tumor antigen peptides were added to the culture medium at 10 µM to stimulate the peripheral blood lymphocytes. After one week, the above tumor antigen peptide was added to attain 10 µM together with about 2×10$^5$ cells of X-radiated (50 Gy) peripheral blood lymphocytes for the second stimulation. After additional one week, the third stimulation was conducted in a similar manner. Cultured lymphocytes were harvested one week after the third stimulation. Using as target cells (1×10$^4$ cells) MT-2, which is an HLA-A2402-positive leukemia T cell line expressing SART-3, and RPMI8402, which is an HLA-A2402-negative leukemia T cell line expressing SART-3, the amount of IFN-γ in the culture medium produced by the above lymphocytes (8×10$^4$ cells) in response to the target cells was measured in accordance with a similar ELISA method to that in Example 1. The results are shown in Table 6.

TABLE 6

| | IFN-γ in Supernatant (pg/ml) | | | |
|---|---|---|---|---|
| Antigen | HD1 | | HD2 | |
| Peptides | MT-2 | RPMI8402 | MT-2 | RPMI8402 |
| "109-118" | 1771 | 159 | 2078 | 28 |
| "315-323" | 2041 | 26 | 974 | 40 |
| None | 552 | 154 | 413 | 69 |

Peripheral blood lymphocytes stimulated with "109-118" and "315-323" peptides reacted to MT-2 (HLA-A24-positive) but not to RPMI8402 (HLA-A24-negative), indicating that CTLs specific for tumor antigen peptide were induced in a HLA-A24-restricted manner.

Likewise, a similar experiment can be conducted using COS-7 cells (ATCC No. CRL1651) or VA-13 cells (RIKEN CELL BANK, The Institute of Physical and Chemical Research) into which an expression plasmid for HLA-A24 cDNA has been introduced and which have been pulsed with the above peptides, instead of MT-2 used in the present experiment (*J. Exp. Med.*, 187:277, 1998).

Example 7

Establishment of Cytotoxic T Lymphocytes (CTLs) Cell Line from Tumor-Infiltrating Lymphocytes (TILs) Derived from Colon Cancer TILs from a surgical sample taken from a patient with sigmoid colon cancer (HLA-A0207-positive) were cultured on 24-well plate in a culture medium consisting of 45% RPMI, 45% AIM-V (GIBCO BRL), and 10% FCS supplemented with 100 U/ml interleukin-2 and 0.1 mM NEAA (GIBCO BRL) (hereinafter referred to as lymphocyte medium). During the first two days of the cultivation, an anti-CD3 antibody NU-T3 (Nichirei Corporation) was added to the culture medium at 1 µg/ml. The cultivation was continued for more than 30 days, and a CTL line that is restricted to HLA-A2 was established, the CTL line being named OK-CTL. OK-CTL was deposited at The National Institute of Bioscience and Human Technology, Agency of Industrial Science and Technology (1-1-3 Higashi, Tsukuba, Ibaraki, Japan) (designation of microorganism: OK-CTL; deposition date: Aug. 3, 1999; deposit number: FERM BP-6818).

According to the description in Nakao et al., *Cancer Res.*, 55:4248-4252 (1995), recombinant plasmids were prepared from SW620 cells (ATCC No. CCL-227), in which cDNAs for HLA-A0201 (GenBank Accession No. M84379) was incorporated into an expression vector pCR3 (INVITROGEN). Using, as target cells, transfectants that had been prepared by doubly transfecting a cell line derived from African green monkey kidney, COS-7 (ATCC No. CRL1651) (1×10$^4$ cells) with recombinant plasmid clone K incorporated with the SART-3 gene cDNA, and with a recombinant plasmid incorporated with HLA-A0201 cDNA using a Lipofectin method similar to in Example 1, the amount of IFN-γ produced by 5×10$^4$ OK-CTLs in response to the target cells was measured by ELISA. As control groups, a non-treatment group wherein no plasmid was transfected, and a group wherein recombinant plasmid clone K and the recombinant plasmid incorporated with HLA-A2402 cDNA were doubly transfected were designed. The result is shown in Table 7.

TABLE 7

| Target cells | Amount of IFN-γ Produced by OK-CTL (pg/ml) |
|---|---|
| COS-7 | 653 |
| COS-7 + HLA-A0201 + K | 2401 |
| COS-7 + HLA-A2402 + K | 600 |

OK-CTL reacted more strongly to the target cells doubly transfected with recombinant plasmid clone K incorporated with SART-3 gene cDNA and with the recombinant plasmid incorporated with HLA-A0201 cDNA, and produced more IFN-γ, compared to other target cell groups. This result indicates that the antigen peptides of tumor antigen protein SART-3 is presented on HLA-A0201, and OK-CTL recognizes it, suggesting that SART-3 contains HLA-A2-restricted tumor antigen peptides.

Example 8

Identification of HLA-A2-Restricted Tumor Antigen Peptides

On the basis of the amino acid sequence of tumor antigen protein SART-3 shown in SEQ ID NO:2, peptide sequences consisting of nine or ten amino acid residues that were expected to be capable of binding to HLA-A0201 were searched on the internet using the BIMAS software of NIH. Those examples of the searched peptides are shown in SEQ ID NOs: 25-52. These peptides were synthesized at Biologica Co. by the Fmoc method.

Then, 1×10$^4$ T2 cells, T-B hybridoma cell line that is HLA-A0201 positive and that lacks in an capability to present endogenous peptides were pulsed with each of peptides expected to be capable of binding to HLA-A0201 that had precedently synthesized at 10 μM over two hours. The cells were then cultured with 6×10⁴ OK-CTLs for 18 hours, and the amount of IFN-γ produced by OK-CTL in the culture supernatant was determined by ELISA. The results of this determination are shown in Table 8, which performed on five peptides, that is, a peptide "152-160" comprising the sequence from position 152 to position 160 (SEQ ID NO: 25), a peptide "249-257" comprising the sequence from position 249 to position 257 (SEQ ID NO: 26), a peptide "302-310" comprising the sequence from position 302 to position 310 (SEQ ID NO: 27), a peptide "309-317" comprising the sequence from position 309 to position 317 (SEQ ID NO: 28), and a peptide "386-394" comprising the sequence from position 386 to position 394 (SEQ ID NO: 29), in the amino acid sequence of tumor antigen protein SART-3.

TABLE 8

| Peptides | IFN-γ in the supernatant (pg/ml)* |
|---|---|
| "152-160" | 162 |
| "249-257" | 209 |
| "302-310" | 190 |
| "309-317" | 231 |
| "386-394" | 122 |

*The values are those subtracted by the amount of produced IFN-γ by T2 cells pulsed with no peptide.

KE-4CTLs reacted more strongly to cells pulsed with the peptides, and produced more IFN-γ, compared to cells pulsed with no peptide. This result indicates that the five peptides function as HLA-A2-restricted tumor antigen peptides.

Likewise, a similar experiment can be conducted using COS-7 cells (ATCC No. CRL1651) or VA-13 cells (RIKEN CELL BANK, The Institute of Physical and Chemical Research) into which an expression plasmid for HLA-A0201 cDNA has been introduced instead of the T2 cells as used in the present experiment (*J. Exp. Med.*, 187:277, 1998).

Sequence Listing Free Text

In the amino acid sequence shown in SEQ ID NO: 53, the second amino acid is phenylalanine, tyrosine, methionine, or tryptophan, and the tenth amino acid is phenylalanine, leucine, isoleucine, tryptophan, or methionine.

In the amino acid sequence shown in SEQ ID NO: 54, the second amino acid is phenylalanine, tyrosine, methionine, or tryptophan, and the tenth amino acid is phenylalanine, leucine, isoleucine, tryptophan, or methionine.

In the amino acid sequence shown in SEQ ID NO: 55, the second amino acid is phenylalanine, tyrosine, methionine, or tryptophan, and the ninth amino acid is phenylalanine, leucine, isoleucine, tryptophan, or methionine.

In the amino acid sequence shown in SEQ ID NO: 56, the second amino acid is phenylalanine, tyrosine, methionine, or tryptophan, and the ninth amino acid is phenylalanine, leucine, isoleucine, tryptophan, or methionine.

In the amino acid sequence shown in SEQ ID NO: 57, the second amino acid is phenylalanine, tyrosine, methionine, or tryptophan, and the tenth amino acid is phenylalanine, leucine, isoleucine, tryptophan, or methionine.

In the amino acid sequence shown in SEQ ID NO: 58, the second amino acid is phenylalanine, tyrosine, methionine, or tryptophan, and the ninth amino acid is phenylalanine, leucine, isoleucine, tryptophan, or methionine.

In the amino acid sequence shown in SEQ ID NO: 59, the second amino acid is phenylalanine, tyrosine, methionine, or tryptophan, and the ninth amino acid is phenylalanine, leucine, isoleucine, tryptophan, or methionine.

In the amino acid sequence shown in SEQ ID NO: 60, the second amino acid is leucine, methionine, valine, isoleucine, or glutamine, and the ninth amino acid is valine, or leucine, In the amino acid sequence shown in SEQ ID NO: 61, the second amino acid is leucine, methionine, valine, isoleucine, or glutamine, and the ninth amino acid is valine, or leucine.

In the amino acid sequence shown in SEQ ID NO: 62, the second amino acid is leucine, methionine, valine, isoleucine, or glutamine, and the ninth amino acid is valine, or leucine.

In the amino acid sequence shown in SEQ ID NO: 63, the second amino acid is leucine, methionine, valine, isoleucine, or glutamine, and the ninth amino acid is valine, or leucine.

In the amino acid sequence shown in SEQ ID NO: 64, the second amino acid is leucine, methionine, valine, isoleucine, or glutamine, and the ninth amino acid is valine, or leucine.

INDUSTRIAL APPLICABILITY

According to the present invention, a novel tumor antigen protein and gene therefor, tumor antigen peptides derived from said tumor antigen protein, and derivatives thereof, as well as medicaments, prophylactics, or diagnostics for tumors using such tumor antigen protein, gene, tumor antigen peptides, or derivatives thereof in vivo or in vitro, can be provided.

The invention claimed is:

1. An isolated peptide consisting of amino acid sequence of SEQ ID NO: 28.

2. The isolated peptide according to claim 1, wherein the peptide is a recombinant polypeptide produced by expressing a recombinant DNA comprising a polynucleotide that encodes the amino acid sequence of SEQ ID NO: 28.

3. A pharmaceutical composition that comprises as an active ingredient the peptide according to claim 1.

4. The pharmaceutical composition according to claim 3, wherein the peptide is a recombinant polypeptide produced by expressing a recombinant DNA comprising a polynucleotide that encodes amino acid sequence of SEQ ID NO: 28.

5. A diagnostic agent that comprises the peptide according to claim 1.

6. The diagnostic agent according to claim 5, wherein the peptide is a recombinant polypeptide produced by expressing a recombinant DNA comprising a polynucleotide that encodes amino acid sequence of SEQ ID NO: 28.

* * * * *

SEQUENCE LISTING

```
<160> NUMBER OF SEQ ID NOS: 64

<210> SEQ ID NO 1
<211> LENGTH: 3798
<212> TYPE: DNA
<213> ORGANISM: Homo sapiens
<220> FEATURE:
<221> NAME/KEY: CDS
<222> LOCATION: (12)..(2900)
<223> OTHER INFORMATION:

<400> SEQUENCE: 1
ccacgcgtcc g atg gcg act gcg gcc gaa acc tcg gct tca gaa ccc gag      50
            Met Ala Thr Ala Ala Glu Thr Ser Ala Ser Glu Pro Glu
            1               5                   10 gct gag tcc aag gct ggg ccc aag gct gac gga gag gag gat gag gtt       98
Ala Glu Ser Lys Ala Gly Pro Lys Ala Asp Gly Glu Glu Asp Glu Val
```

```
            15                  20                  25
aag gcg gct agg aca agg aga aag gtg tta tcg cgg gct gtg gcc gct    146
Lys Ala Ala Arg Thr Arg Arg Lys Val Leu Ser Arg Ala Val Ala Ala
 30                  35                  40                  45 gcg aca tac aag acc atg ggg cca gcg tgg gat cag cag gag gaa ggc    194
Ala Thr Tyr Lys Thr Met Gly Pro Ala Trp Asp Gln Gln Glu Glu Gly
                 50                  55                  60 gtg agc gag agc gat ggg gat gag tac gcc atg gct tcc tcc gcg gag    242
Val Ser Glu Ser Asp Gly Asp Glu Tyr Ala Met Ala Ser Ser Ala Glu
             65                  70                  75 agc tcc ccc ggg gag tac gag tgg gaa tat gac gaa gag gag gag aaa    290
Ser Ser Pro Gly Glu Tyr Glu Trp Glu Tyr Asp Glu Glu Glu Glu Lys
         80                  85                  90 aac cag ctg gag att gag aga ctg gag gag cag ttg tct atc aac gtc    338
Asn Gln Leu Glu Ile Glu Arg Leu Glu Glu Gln Leu Ser Ile Asn Val
     95                 100                 105 tat gac tac aac tgc cat gtg gac ttg atc aga ctg ctc agg ctg gaa    386
Tyr Asp Tyr Asn Cys His Val Asp Leu Ile Arg Leu Leu Arg Leu Glu
110                 115                 120                 125 ggg gag ctt acc aag gtg agg atg gcc cgc cag aag atg agt gaa atc    434
Gly Glu Leu Thr Lys Val Arg Met Ala Arg Gln Lys Met Ser Glu Ile
                130                 135                 140 ttt ccc ttg act gaa gag ctc tgg ctg gag tgg ctg cat gac gag atc    482
Phe Pro Leu Thr Glu Glu Leu Trp Leu Glu Trp Leu His Asp Glu Ile
            145                 150                 155 agc atg gcc cag gat ggc ctg gac aga gag cac gtg tat gac ctc ttt    530
Ser Met Ala Gln Asp Gly Leu Asp Arg Glu His Val Tyr Asp Leu Phe
        160                 165                 170 gag aaa gcc gtg aag gat tac att tgt cct aac att tgg cta gag tat    578
Glu Lys Ala Val Lys Asp Tyr Ile Cys Pro Asn Ile Trp Leu Glu Tyr
    175                 180                 185 ggc cag tac tca gtt ggt ggg att ggt cag aaa ggt ggc ctt gag aaa    626
Gly Gln Tyr Ser Val Gly Gly Ile Gly Gln Lys Gly Gly Leu Glu Lys
190                 195                 200                 205 gtt cgc tcc gtg ttt gaa agg gct ctc tcg tct gtt ggt tta cat atg    674
Val Arg Ser Val Phe Glu Arg Ala Leu Ser Ser Val Gly Leu His Met
                210                 215                 220 acc aaa gga ctc gcc ctc tgg gag gct tac cga gag ttt gaa agt gcg    722
Thr Lys Gly Leu Ala Leu Trp Glu Ala Tyr Arg Glu Phe Glu Ser Ala
            225                 230                 235 att gtg gaa gct gct cgg ctt gag aaa gtc cac agt ctt ttc cgg cga    770
Ile Val Glu Ala Ala Arg Leu Glu Lys Val His Ser Leu Phe Arg Arg
        240                 245                 250 cag ttg gcg atc cca ctc tat gat atg gag gcc aca ttt gca gag tat    818
Gln Leu Ala Ile Pro Leu Tyr Asp Met Glu Ala Thr Phe Ala Glu Tyr
    255                 260                 265 gaa gaa tgg tca gaa gac cca ata cca gag tca gta att cag aac tat    866
Glu Glu Trp Ser Glu Asp Pro Ile Pro Glu Ser Val Ile Gln Asn Tyr
270                 275                 280                 285 aac aaa gca cta cag cag ctg gag aaa tat aaa ccc tat gaa gaa gca    914
Asn Lys Ala Leu Gln Gln Leu Glu Lys Tyr Lys Pro Tyr Glu Glu Ala
                290                 295                 300 ctg ttg cag gca gag gca cca agg ctg gca gaa tat caa gca tat atc    962
Leu Leu Gln Ala Glu Ala Pro Arg Leu Ala Glu Tyr Gln Ala Tyr Ile
            305                 310                 315 gat ttt gag atg aaa att ggc gat cct gct cgc att cag ttg atc ttt    1010
Asp Phe Glu Met Lys Ile Gly Asp Pro Ala Arg Ile Gln Leu Ile Phe
        320                 325                 330 gag cgc gcc ctg gtc gag aac tgc ctt gtc cca gac tta tgg atc cgt    1058
Glu Arg Ala Leu Val Glu Asn Cys Leu Val Pro Asp Leu Trp Ile Arg
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 335 |     |     |     | 340 |     |     |     |     | 345 |     |     |     |     |     |      |
| tac | agt | cag | tac | cta | gat | cga | caa | ctg | aaa | gta | aag | gat | ttg | gtt | tta | 1106 |
| Tyr | Ser | Gln | Tyr | Leu | Asp | Arg | Gln | Leu | Lys | Val | Lys | Asp | Leu | Val | Leu |      |
| 350 |     |     |     |     | 355 |     |     |     |     | 360 |     |     |     |     | 365 |      |
| tct | gta | cat | aac | cgc | gct | att | aga | aac | tgc | ccc | tgg | aca | gtt | gcc | tta | 1154 |
| Ser | Val | His | Asn | Arg | Ala | Ile | Arg | Asn | Cys | Pro | Trp | Thr | Val | Ala | Leu |      |
|     |     |     |     | 370 |     |     |     |     | 375 |     |     |     |     | 380 |     |      |
| tgg | agt | cgg | tac | ctc | ttg | gcc | atg | gag | aga | cat | gga | gtt | gat | cat | caa | 1202 |
| Trp | Ser | Arg | Tyr | Leu | Leu | Ala | Met | Glu | Arg | His | Gly | Val | Asp | His | Gln |      |
|     |     | 385 |     |     |     |     | 390 |     |     |     |     | 395 |     |     |     |      |
| gta | att | tct | gta | acc | ttc | gag | aaa | gct | ttg | aat | gcc | ggc | ttc | atc | cag | 1250 |
| Val | Ile | Ser | Val | Thr | Phe | Glu | Lys | Ala | Leu | Asn | Ala | Gly | Phe | Ile | Gln |      |
| 400 |     |     |     |     | 405 |     |     |     |     | 410 |     |     |     |     |     |      |
| gcc | act | gat | tat | gtg | gag | att | tgg | cag | gca | tac | ctt | gat | tac | ctg | agg | 1298 |
| Ala | Thr | Asp | Tyr | Val | Glu | Ile | Trp | Gln | Ala | Tyr | Leu | Asp | Tyr | Leu | Arg |      |
|     | 415 |     |     |     |     | 420 |     |     |     |     | 425 |     |     |     |     |      |
| aga | agg | gtt | gat | ttc | aaa | caa | gac | tcc | agt | aaa | gag | ctg | gag | gag | ttg | 1346 |
| Arg | Arg | Val | Asp | Phe | Lys | Gln | Asp | Ser | Ser | Lys | Glu | Leu | Glu | Glu | Leu |      |
| 430 |     |     |     |     | 435 |     |     |     |     | 440 |     |     |     |     | 445 |      |
| agg | gcc | gcc | ttt | act | cgt | gcc | ttg | gag | tat | ctg | aag | cag | gag | gtg | gaa | 1394 |
| Arg | Ala | Ala | Phe | Thr | Arg | Ala | Leu | Glu | Tyr | Leu | Lys | Gln | Glu | Val | Glu |      |
|     |     |     |     | 450 |     |     |     |     | 455 |     |     |     |     | 460 |     |      |
| gag | cgt | ttc | aat | gag | agt | ggt | gat | cca | agc | tgc | gtg | att | atg | cag | aac | 1442 |
| Glu | Arg | Phe | Asn | Glu | Ser | Gly | Asp | Pro | Ser | Cys | Val | Ile | Met | Gln | Asn |      |
|     |     | 465 |     |     |     |     | 470 |     |     |     |     | 475 |     |     |     |      |
| tgg | gct | agg | att | gag | gct | cga | ctg | tgc | aat | aac | atg | cag | aaa | gct | cgg | 1490 |
| Trp | Ala | Arg | Ile | Glu | Ala | Arg | Leu | Cys | Asn | Asn | Met | Gln | Lys | Ala | Arg |      |
|     | 480 |     |     |     |     | 485 |     |     |     |     | 490 |     |     |     |     |      |
| gaa | ctc | tgg | gat | agc | atc | atg | acc | aga | gga | aat | gcc | aag | tac | gcc | aac | 1538 |
| Glu | Leu | Trp | Asp | Ser | Ile | Met | Thr | Arg | Gly | Asn | Ala | Lys | Tyr | Ala | Asn |      |
| 495 |     |     |     |     | 500 |     |     |     |     | 505 |     |     |     |     |     |      |
| atg | tgg | cta | gag | tat | tac | aac | ctg | gaa | aga | gct | cat | ggt | gac | acc | cag | 1586 |
| Met | Trp | Leu | Glu | Tyr | Tyr | Asn | Leu | Glu | Arg | Ala | His | Gly | Asp | Thr | Gln |      |
| 510 |     |     |     |     | 515 |     |     |     |     | 520 |     |     |     |     | 525 |      |
| cac | tgc | cgg | aag | gct | ctg | cac | cgg | gcc | gtc | cag | tgc | acc | agt | gac | tac | 1634 |
| His | Cys | Arg | Lys | Ala | Leu | His | Arg | Ala | Val | Gln | Cys | Thr | Ser | Asp | Tyr |      |
|     |     |     |     | 530 |     |     |     |     | 535 |     |     |     |     | 540 |     |      |
| cca | gag | cac | gtc | tgc | gaa | gtg | tta | ctc | acc | atg | gag | agg | aca | gaa | ggt | 1682 |
| Pro | Glu | His | Val | Cys | Glu | Val | Leu | Leu | Thr | Met | Glu | Arg | Thr | Glu | Gly |      |
|     |     |     | 545 |     |     |     |     | 550 |     |     |     |     | 555 |     |     |      |
| tct | tta | gaa | gat | tgg | gat | ata | gct | gtt | cag | aaa | act | gaa | acc | cga | tta | 1730 |
| Ser | Leu | Glu | Asp | Trp | Asp | Ile | Ala | Val | Gln | Lys | Thr | Glu | Thr | Arg | Leu |      |
|     |     | 560 |     |     |     |     | 565 |     |     |     |     | 570 |     |     |     |      |
| gct | cgt | gtc | aat | gag | cag | aga | atg | aag | gct | gca | gag | aag | gaa | gca | gcc | 1778 |
| Ala | Arg | Val | Asn | Glu | Gln | Arg | Met | Lys | Ala | Ala | Glu | Lys | Glu | Ala | Ala |      |
|     | 575 |     |     |     |     | 580 |     |     |     |     | 585 |     |     |     |     |      |
| ctt | gtg | cag | caa | gaa | gaa | aag | gct | gaa | caa | cgg | aaa | aga | gct | cgg | 1826 |      |
| Leu | Val | Gln | Gln | Glu | Glu | Lys | Ala | Glu | Gln | Arg | Lys | Arg | Ala | Arg |     |      |
| 590 |     |     |     |     | 595 |     |     |     |     | 600 |     |     |     | 605 |     |      |
| gct | gag | aag | aaa | gcg | tta | aaa | aag | aag | aaa | aag | atc | aga | ggc | cca | gag | 1874 |
| Ala | Glu | Lys | Lys | Ala | Leu | Lys | Lys | Lys | Lys | Lys | Ile | Arg | Gly | Pro | Glu |      |
|     |     |     |     | 610 |     |     |     |     | 615 |     |     |     |     | 620 |     |      |
| aag | cgc | gga | gca | gat | gag | gac | gat | gag | aaa | gag | tgg | ggc | gat | gat | gaa | 1922 |
| Lys | Arg | Gly | Ala | Asp | Glu | Asp | Asp | Glu | Lys | Glu | Trp | Gly | Asp | Asp | Glu |      |
|     |     | 625 |     |     |     |     | 630 |     |     |     |     | 635 |     |     |     |      |
| gaa | gag | cag | cct | tcc | aaa | cgc | aga | agg | gtc | gag | aac | agc | atc | cct | gca | 1970 |
| Glu | Glu | Gln | Pro | Ser | Lys | Arg | Arg | Arg | Val | Glu | Asn | Ser | Ile | Pro | Ala |      |
|     |     | 640 |     |     |     |     | 645 |     |     |     |     | 650 |     |     |     |      |
| gct | gga | gaa | aca | caa | aat | gta | gaa | gta | gca | gca | ggg | ccc | gct | ggg | aaa | 2018 |
| Ala | Gly | Glu | Thr | Gln | Asn | Val | Glu | Val | Ala | Ala | Gly | Pro | Ala | Gly | Lys |      |

```
                655                 660                 665
tgt gct gcc gta gat gtg gag ccc cct tcg aag cag aag gag aag gca    2066
Cys Ala Ala Val Asp Val Glu Pro Pro Ser Lys Gln Lys Glu Lys Ala
670                 675                 680                 685 gcc tcc ctg aag agg gac atg ccc aag gtg ctg cac gac agc agc aag    2114
Ala Ser Leu Lys Arg Asp Met Pro Lys Val Leu His Asp Ser Ser Lys
                690                 695                 700 gac agc atc acc gtc ttt gtc agc aac ctg ccc tac agc atg cag gag    2162
Asp Ser Ile Thr Val Phe Val Ser Asn Leu Pro Tyr Ser Met Gln Glu
    705                 710                 715 ccg gac acg aag ctc agg cca ctc ttc gag gcc tgt ggg gag gtg gtc    2210
Pro Asp Thr Lys Leu Arg Pro Leu Phe Glu Ala Cys Gly Glu Val Val
720                 725                 730 cag atc cga ccc atc ttc agc aac cgt ggg gat ttc cga ggt tac tgc    2258
Gln Ile Arg Pro Ile Phe Ser Asn Arg Gly Asp Phe Arg Gly Tyr Cys
735                 740                 745 tac gtg gag ttt aaa gaa gag aaa tca gcc ctt cag gca ctg gag atg    2306
Tyr Val Glu Phe Lys Glu Glu Lys Ser Ala Leu Gln Ala Leu Glu Met
750                 755                 760                 765 gac cgg aaa agt gta gaa ggg agg cca atg ttt gtt tcc ccc tgt gtg    2354
Asp Arg Lys Ser Val Glu Gly Arg Pro Met Phe Val Ser Pro Cys Val
                770                 775                 780 gat aag agc aaa aac ccc gat ttt aag gtg ttc agg tac agc act tcc    2402
Asp Lys Ser Lys Asn Pro Asp Phe Lys Val Phe Arg Tyr Ser Thr Ser
                785                 790                 795 cta gag aaa cac aag ctg ttc atc tca ggc ctg cct ttc tcc tgt act    2450
Leu Glu Lys His Lys Leu Phe Ile Ser Gly Leu Pro Phe Ser Cys Thr
                800                 805                 810 aaa gag gaa cta gaa gaa atc tgt aag gct cat ggc acc gtg aag gac    2498
Lys Glu Glu Leu Glu Glu Ile Cys Lys Ala His Gly Thr Val Lys Asp
815                 820                 825 ctc agg ctg gtc acc aac cgg gct ggc aaa cca aag ggc ctg gcc tac    2546
Leu Arg Leu Val Thr Asn Arg Ala Gly Lys Pro Lys Gly Leu Ala Tyr
830                 835                 840                 845 gtg gag tat gaa aat gaa tcc cag gcg tcg cag gct gtg atg aag atg    2594
Val Glu Tyr Glu Asn Glu Ser Gln Ala Ser Gln Ala Val Met Lys Met
                850                 855                 860 gac ggc atg act atc aaa gag aac atc atc aaa gtg gca atc agc aac    2642
Asp Gly Met Thr Ile Lys Glu Asn Ile Ile Lys Val Ala Ile Ser Asn
                865                 870                 875 cct cct cag agg aaa gtt cca gag aag cca gag acc agg aag gca cca    2690
Pro Pro Gln Arg Lys Val Pro Glu Lys Pro Glu Thr Arg Lys Ala Pro
                880                 885                 890 ggt ggc ccc atg ctt ttg ccg cag aca tac gga gcg agg ggg aag gga    2738
Gly Gly Pro Met Leu Leu Pro Gln Thr Tyr Gly Ala Arg Gly Lys Gly
895                 900                 905 agg acg cag ctg tct cta ctg cct cgt gcc ctg cag cgc cca agt gct    2786
Arg Thr Gln Leu Ser Leu Leu Pro Arg Ala Leu Gln Arg Pro Ser Ala
910                 915                 920                 925 gca gct cct cag gct gag aac ggc cct gcc gcg gct cct gca gtt gcc    2834
Ala Ala Pro Gln Ala Glu Asn Gly Pro Ala Ala Ala Pro Ala Val Ala
                930                 935                 940 gcc cca gca gcc acc gag gca ccc aag atg tcc aat gcc gat ttt gcc    2882
Ala Pro Ala Ala Thr Glu Ala Pro Lys Met Ser Asn Ala Asp Phe Ala
                945                 950                 955 aag ctg ttt ctg aga aag tgaacgggac gctgggagac aggaaatgcc            2930
Lys Leu Phe Leu Arg Lys
                960 ttacttcact ctggcccggc ggacctccca ccacccagca gtgcactggg gatggacagg   2990
```

-continued

```
cctggtgtgc tgcgtgctcg caaccacaga tggctcctcg gctttagaca gaaaggggaa   3050
ggggttctaa gtcaagagcc tttcagtgct ccctcatatt gagggcagtg gcagaaaagt   3110
gaccactctg caggctgggc ccaggatgtg gtgtcctgag atagttttgt atcttaaaga   3170
ctgaggcaca gaagcgaaac gagaacacac tgtttttgag acacagttgt ccaaatgttt   3230
ctggccagct ccggccccctt tttgtatgac acttctcttc caccctgcac agcacatgtg   3290
cccgtcattc ttttaattt  aaaagatgaa atggcagatg ctagtaattc acagaatggc   3350
ctcttgtggg ggtgggtctg agggaagtca gctataaaac atttgctgga gttttgttca   3410
atggggctgt gcattttat  attatgtgtt tgtaaatgac atgtcagccc ttgtttcatg   3470
tttcctaaaa gcagaatatt tgcaacattt gttttgtata ggaattattt gtgccacctg   3530
ctgtggactt ttttctttgc ctagtgacta gtgacctgtg ttgtctaaac atgagtttca   3590 gcccttggt  tttgtttaat accatgtcaa atgcaaactt caattctccc catttagctt   3650
tattaaactg acgttctctt caaaacttct tgctgaatgg tactcagatg tgcattcaca   3710
tacagatgtg ttttgaagtg ggtgtacctt gctttaccta atagatgtgt aaatagaact   3770
tttgtaagtc aaaaaaaaaa aaaaaaaa                                      3798
```

<210> SEQ ID NO 2
<211> LENGTH: 963
<212> TYPE: PRT
<213> ORGANISM: Homo sapiens

<400> SEQUENCE: 2

```
Met Ala Thr Ala Ala Glu Thr Ser Ala Ser Glu Pro Glu Ala Glu Ser
1               5                   10                  15

Lys Ala Gly Pro Lys Ala Asp Gly Glu Glu Asp Glu Val Lys Ala Ala
            20                  25                  30

Arg Thr Arg Arg Lys Val Leu Ser Arg Ala Val Ala Ala Ala Thr Tyr
        35                  40                  45

Lys Thr Met Gly Pro Ala Trp Asp Gln Gln Glu Gly Val Ser Glu
    50                  55                  60

Ser Asp Gly Asp Glu Tyr Ala Met Ala Ser Ser Ala Glu Ser Ser Pro
65                  70                  75                  80

Gly Glu Tyr Glu Trp Glu Tyr Asp Glu Glu Glu Lys Asn Gln Leu
                85                  90                  95

Glu Ile Glu Arg Leu Glu Glu Gln Leu Ser Ile Asn Val Tyr Asp Tyr
            100                 105                 110

Asn Cys His Val Asp Leu Ile Arg Leu Leu Arg Leu Glu Gly Glu Leu
        115                 120                 125

Thr Lys Val Arg Met Ala Arg Gln Lys Met Ser Glu Ile Phe Pro Leu
    130                 135                 140

Thr Glu Glu Leu Trp Leu Glu Trp Leu His Asp Glu Ile Ser Met Ala
145                 150                 155                 160

Gln Asp Gly Leu Asp Arg Glu His Val Tyr Asp Leu Phe Glu Lys Ala
                165                 170                 175

Val Lys Asp Tyr Ile Cys Pro Asn Ile Trp Leu Glu Tyr Gly Gln Tyr
            180                 185                 190

Ser Val Gly Gly Ile Gly Gln Lys Gly Gly Leu Glu Lys Val Arg Ser
        195                 200                 205

Val Phe Glu Arg Ala Leu Ser Ser Val Gly Leu His Met Thr Lys Gly
    210                 215                 220

Leu Ala Leu Trp Glu Ala Tyr Arg Glu Phe Glu Ser Ala Ile Val Glu
225                 230                 235                 240
```

```
Ala Ala Arg Leu Glu Lys Val His Ser Leu Phe Arg Arg Gln Leu Ala
            245                 250                 255

Ile Pro Leu Tyr Asp Met Glu Ala Thr Phe Ala Glu Tyr Glu Glu Trp
            260                 265                 270

Ser Glu Asp Pro Ile Pro Glu Ser Val Ile Gln Asn Tyr Asn Lys Ala
            275                 280                 285

Leu Gln Gln Leu Glu Lys Tyr Lys Pro Tyr Glu Glu Ala Leu Leu Gln
            290                 295                 300

Ala Glu Ala Pro Arg Leu Ala Glu Tyr Gln Ala Tyr Ile Asp Phe Glu
305                 310                 315                 320

Met Lys Ile Gly Asp Pro Ala Arg Ile Gln Leu Ile Phe Glu Arg Ala
            325                 330                 335

Leu Val Glu Asn Cys Leu Val Pro Asp Leu Trp Ile Arg Tyr Ser Gln
            340                 345                 350

Tyr Leu Asp Arg Gln Leu Lys Val Lys Asp Leu Val Leu Ser Val His
            355                 360                 365

Asn Arg Ala Ile Arg Asn Cys Pro Trp Thr Val Ala Leu Trp Ser Arg
            370                 375                 380

Tyr Leu Leu Ala Met Glu Arg His Gly Val Asp His Gln Val Ile Ser
385                 390                 395                 400

Val Thr Phe Glu Lys Ala Leu Asn Ala Gly Phe Ile Gln Ala Thr Asp
            405                 410                 415

Tyr Val Glu Ile Trp Gln Ala Tyr Leu Asp Tyr Leu Arg Arg Arg Val
            420                 425                 430

Asp Phe Lys Gln Asp Ser Ser Lys Glu Leu Glu Leu Arg Ala Ala
            435                 440                 445

Phe Thr Arg Ala Leu Glu Tyr Leu Lys Gln Glu Val Glu Glu Arg Phe
            450                 455                 460

Asn Glu Ser Gly Asp Pro Ser Cys Val Ile Met Gln Asn Trp Ala Arg
465                 470                 475                 480

Ile Glu Ala Arg Leu Cys Asn Asn Met Gln Lys Ala Arg Glu Leu Trp
            485                 490                 495

Asp Ser Ile Met Thr Arg Gly Asn Ala Lys Tyr Ala Asn Met Trp Leu
            500                 505                 510

Glu Tyr Tyr Asn Leu Glu Arg Ala His Gly Asp Thr Gln His Cys Arg
            515                 520                 525

Lys Ala Leu His Arg Ala Val Gln Cys Thr Ser Asp Tyr Pro Glu His
            530                 535                 540

Val Cys Glu Val Leu Leu Thr Met Glu Arg Thr Glu Gly Ser Leu Glu
545                 550                 555                 560

Asp Trp Asp Ile Ala Val Gln Lys Thr Glu Thr Arg Leu Ala Arg Val
            565                 570                 575

Asn Glu Gln Arg Met Lys Ala Ala Glu Lys Ala Ala Leu Val Gln
            580                 585                 590

Gln Glu Glu Glu Lys Ala Glu Gln Arg Lys Arg Ala Arg Ala Glu Lys
            595                 600                 605

Lys Ala Leu Lys Lys Lys Lys Ile Arg Gly Pro Glu Lys Arg Gly
            610                 615                 620

Ala Asp Glu Asp Glu Lys Glu Trp Gly Asp Glu Glu Glu Gln
625                 630                 635                 640

Pro Ser Lys Arg Arg Val Glu Asn Ser Ile Pro Ala Ala Gly Glu
            645                 650                 655

Thr Gln Asn Val Glu Val Ala Ala Gly Pro Ala Gly Lys Cys Ala Ala
```

```
                     660                 665                 670
Val Asp Val Glu Pro Pro Ser Lys Gln Lys Glu Lys Ala Ala Ser Leu
            675                 680                 685

Lys Arg Asp Met Pro Lys Val Leu His Asp Ser Ser Lys Asp Ser Ile
        690                 695                 700

Thr Val Phe Val Ser Asn Leu Pro Tyr Ser Met Gln Glu Pro Asp Thr
705                 710                 715                 720

Lys Leu Arg Pro Leu Phe Glu Ala Cys Gly Glu Val Val Gln Ile Arg
                725                 730                 735

Pro Ile Phe Ser Asn Arg Gly Asp Phe Arg Gly Tyr Cys Tyr Val Glu
            740                 745                 750

Phe Lys Glu Glu Lys Ser Ala Leu Gln Ala Leu Glu Met Asp Arg Lys
        755                 760                 765

Ser Val Glu Gly Arg Pro Met Phe Val Ser Pro Cys Val Asp Lys Ser
770                 775                 780

Lys Asn Pro Asp Phe Lys Val Phe Arg Tyr Ser Thr Ser Leu Glu Lys
785                 790                 795                 800

His Lys Leu Phe Ile Ser Gly Leu Pro Phe Ser Cys Thr Lys Glu Glu
                805                 810                 815

Leu Glu Glu Ile Cys Lys Ala His Gly Thr Val Lys Asp Leu Arg Leu
            820                 825                 830

Val Thr Asn Arg Ala Gly Lys Pro Lys Gly Leu Ala Tyr Val Glu Tyr
        835                 840                 845

Glu Asn Glu Ser Gln Ala Ser Gln Ala Val Met Lys Met Asp Gly Met
850                 855                 860

Thr Ile Lys Glu Asn Ile Ile Lys Val Ala Ile Ser Asn Pro Pro Gln
865                 870                 875                 880

Arg Lys Val Pro Glu Lys Pro Glu Thr Arg Lys Ala Pro Gly Gly Pro
                885                 890                 895

Met Leu Pro Gln Thr Tyr Gly Ala Arg Gly Lys Gly Arg Thr Gln
            900                 905                 910

Leu Ser Leu Leu Pro Arg Ala Leu Gln Arg Pro Ser Ala Ala Pro
        915                 920                 925

Gln Ala Glu Asn Gly Pro Ala Ala Pro Ala Val Ala Pro Ala
930                 935                 940

Ala Thr Glu Ala Pro Lys Met Ser Asn Ala Asp Phe Ala Lys Leu Phe
945                 950                 955                 960

Leu Arg Lys

<210> SEQ ID NO 3
<211> LENGTH: 10
<212> TYPE: PRT
<213> ORGANISM: Homo sapiens

<400> SEQUENCE: 3

Val Tyr Asp Tyr Asn Cys His Val Asp Leu
1               5                   10

<210> SEQ ID NO 4
<211> LENGTH: 10
<212> TYPE: PRT
<213> ORGANISM: Homo sapiens

<400> SEQUENCE: 4

Leu Phe Glu Lys Ala Val Lys Asp Tyr Ile
1               5                   10
```

```
<210> SEQ ID NO 5
<211> LENGTH: 9
<212> TYPE: PRT
<213> ORGANISM: Homo sapiens

<400> SEQUENCE: 5

Asn Tyr Asn Lys Ala Leu Gln Gln Leu
1               5

<210> SEQ ID NO 6
<211> LENGTH: 9
<212> TYPE: PRT
<213> ORGANISM: Homo sapiens

<400> SEQUENCE: 6

Ala Tyr Ile Asp Phe Glu Met Lys Ile
1               5

<210> SEQ ID NO 7
<211> LENGTH: 10
<212> TYPE: PRT
<213> ORGANISM: Homo sapiens

<400> SEQUENCE: 7

Asp Tyr Val Glu Ile Trp Gln Ala Tyr Leu
1               5                   10

<210> SEQ ID NO 8
<211> LENGTH: 9
<212> TYPE: PRT
<213> ORGANISM: Homo sapiens

<400> SEQUENCE: 8

Asp Tyr Leu Arg Arg Arg Val Asp Phe
1               5

<210> SEQ ID NO 9
<211> LENGTH: 9
<212> TYPE: PRT
<213> ORGANISM: Homo sapiens

<400> SEQUENCE: 9

Ala Phe Thr Arg Ala Leu Glu Tyr Leu
1               5

<210> SEQ ID NO 10
<211> LENGTH: 9
<212> TYPE: PRT
<213> ORGANISM: Homo sapiens

<400> SEQUENCE: 10

Asp Tyr Asn Cys His Val Asp Leu Ile
1               5

<210> SEQ ID NO 11
<211> LENGTH: 10
<212> TYPE: PRT
<213> ORGANISM: Homo sapiens

<400> SEQUENCE: 11

Ile Phe Pro Leu Thr Glu Glu Leu Trp Leu
1               5                   10

<210> SEQ ID NO 12
<211> LENGTH: 9
```

```
<212> TYPE: PRT
<213> ORGANISM: Homo sapiens

<400> SEQUENCE: 12

Asp Tyr Ile Cys Pro Asn Ile Trp Leu
1               5

<210> SEQ ID NO 13
<211> LENGTH: 10
<212> TYPE: PRT
<213> ORGANISM: Homo sapiens

<400> SEQUENCE: 13

Glu Tyr Gly Gln Tyr Ser Val Gly Gly Ile
1               5                   10

<210> SEQ ID NO 14
<211> LENGTH: 9
<212> TYPE: PRT
<213> ORGANISM: Homo sapiens

<400> SEQUENCE: 14

Ala Tyr Arg Glu Phe Glu Ser Ala Ile
1               5

<210> SEQ ID NO 15
<211> LENGTH: 10
<212> TYPE: PRT
<213> ORGANISM: Homo sapiens

<400> SEQUENCE: 15

Leu Phe Arg Arg Gln Leu Ala Ile Pro Leu
1               5                   10

<210> SEQ ID NO 16
<211> LENGTH: 10
<212> TYPE: PRT
<213> ORGANISM: Homo sapiens

<400> SEQUENCE: 16

Glu Tyr Glu Glu Trp Ser Glu Asp Pro Ile
1               5                   10

<210> SEQ ID NO 17
<211> LENGTH: 9
<212> TYPE: PRT
<213> ORGANISM: Homo sapiens

<400> SEQUENCE: 17

Lys Tyr Lys Pro Tyr Glu Glu Ala Leu
1               5

<210> SEQ ID NO 18
<211> LENGTH: 10
<212> TYPE: PRT
<213> ORGANISM: Homo sapiens

<400> SEQUENCE: 18

Arg Tyr Ser Gln Tyr Leu Asp Arg Gln Leu
1               5                   10

<210> SEQ ID NO 19
<211> LENGTH: 10
<212> TYPE: PRT
<213> ORGANISM: Homo sapiens
```

```
<400> SEQUENCE: 19

Thr Phe Glu Lys Ala Leu Asn Ala Gly Phe
1               5                   10

<210> SEQ ID NO 20
<211> LENGTH: 10
<212> TYPE: PRT
<213> ORGANISM: Homo sapiens

<400> SEQUENCE: 20

Asp Phe Lys Gln Asp Ser Ser Lys Glu Leu
1               5                   10

<210> SEQ ID NO 21
<211> LENGTH: 10
<212> TYPE: PRT
<213> ORGANISM: Homo sapiens

<400> SEQUENCE: 21

Asp Tyr Pro Glu His Val Cys Glu Val Leu
1               5                   10

<210> SEQ ID NO 22
<211> LENGTH: 10
<212> TYPE: PRT
<213> ORGANISM: Homo sapiens

<400> SEQUENCE: 22

Asp Phe Arg Gly Tyr Cys Tyr Val Glu Phe
1               5                   10

<210> SEQ ID NO 23
<211> LENGTH: 9
<212> TYPE: PRT
<213> ORGANISM: Homo sapiens

<400> SEQUENCE: 23

Glu Phe Lys Glu Glu Lys Ser Ala Leu
1               5

<210> SEQ ID NO 24
<211> LENGTH: 9
<212> TYPE: PRT
<213> ORGANISM: Homo sapiens

<400> SEQUENCE: 24

Pro Phe Ser Cys Thr Lys Glu Glu Leu
1               5

<210> SEQ ID NO 25
<211> LENGTH: 9
<212> TYPE: PRT
<213> ORGANISM: Homo sapiens

<400> SEQUENCE: 25

Trp Leu His Asp Glu Ile Ser Met Ala
1               5

<210> SEQ ID NO 26
<211> LENGTH: 9
<212> TYPE: PRT
<213> ORGANISM: Homo sapiens

<400> SEQUENCE: 26

Ser Leu Phe Arg Arg Gln Leu Ala Ile
```

```
<210> SEQ ID NO 27
<211> LENGTH: 9
<212> TYPE: PRT
<213> ORGANISM: Homo sapiens

<400> SEQUENCE: 27

Leu Leu Gln Ala Glu Ala Pro Arg Leu
1               5

<210> SEQ ID NO 28
<211> LENGTH: 9
<212> TYPE: PRT
<213> ORGANISM: Homo sapiens

<400> SEQUENCE: 28

Arg Leu Ala Glu Tyr Gln Ala Tyr Ile
1               5

<210> SEQ ID NO 29
<211> LENGTH: 9
<212> TYPE: PRT
<213> ORGANISM: Homo sapiens

<400> SEQUENCE: 29

Leu Leu Ala Met Glu Arg His Gly Val
1               5

<210> SEQ ID NO 30
<211> LENGTH: 9
<212> TYPE: PRT
<213> ORGANISM: Homo sapiens

<400> SEQUENCE: 30

Asn Val Tyr Asp Tyr Asn Cys His Val
1               5

<210> SEQ ID NO 31
<211> LENGTH: 9
<212> TYPE: PRT
<213> ORGANISM: Homo sapiens

<400> SEQUENCE: 31

Lys Met Ser Glu Ile Phe Pro Leu Thr
1               5

<210> SEQ ID NO 32
<211> LENGTH: 9
<212> TYPE: PRT
<213> ORGANISM: Homo sapiens

<400> SEQUENCE: 32

Trp Leu Glu Tyr Gly Gln Tyr Ser Val
1               5

<210> SEQ ID NO 33
<211> LENGTH: 10
<212> TYPE: PRT
<213> ORGANISM: Homo sapiens

<400> SEQUENCE: 33

Ser Val Phe Glu Arg Ala Leu Ser Ser Val
1               5                   10
```

```
<210> SEQ ID NO 34
<211> LENGTH: 10
<212> TYPE: PRT
<213> ORGANISM: Homo sapiens

<400> SEQUENCE: 34

Ala Leu Leu Gln Ala Glu Ala Pro Arg Leu
1               5                   10

<210> SEQ ID NO 35
<211> LENGTH: 10
<212> TYPE: PRT
<213> ORGANISM: Homo sapiens

<400> SEQUENCE: 35

Lys Ile Gly Asp Pro Ala Arg Ile Gln Leu
1               5                   10

<210> SEQ ID NO 36
<211> LENGTH: 10
<212> TYPE: PRT
<213> ORGANISM: Homo sapiens

<400> SEQUENCE: 36

Ile Gln Leu Ile Phe Glu Arg Ala Leu Val
1               5                   10

<210> SEQ ID NO 37
<211> LENGTH: 9
<212> TYPE: PRT
<213> ORGANISM: Homo sapiens

<400> SEQUENCE: 37

Gln Leu Ile Phe Glu Arg Ala Leu Val
1               5

<210> SEQ ID NO 38
<211> LENGTH: 10
<212> TYPE: PRT
<213> ORGANISM: Homo sapiens

<400> SEQUENCE: 38

Asp Leu Trp Ile Arg Tyr Ser Gln Tyr Leu
1               5                   10

<210> SEQ ID NO 39
<211> LENGTH: 9
<212> TYPE: PRT
<213> ORGANISM: Homo sapiens

<400> SEQUENCE: 39

Ala Leu Trp Ser Arg Tyr Leu Leu Ala
1               5

<210> SEQ ID NO 40
<211> LENGTH: 10
<212> TYPE: PRT
<213> ORGANISM: Homo sapiens

<400> SEQUENCE: 40

Ala Leu Trp Ser Arg Tyr Leu Leu Ala Met
1               5                   10

<210> SEQ ID NO 41
<211> LENGTH: 10
<212> TYPE: PRT
```

<213> ORGANISM: Homo sapiens

<400> SEQUENCE: 41

Tyr Leu Leu Ala Met Glu Arg His Gly Val
1               5                   10

<210> SEQ ID NO 42
<211> LENGTH: 10
<212> TYPE: PRT
<213> ORGANISM: Homo sapiens

<400> SEQUENCE: 42

Ala Leu Asn Ala Gly Phe Ile Gln Ala Thr
1               5                   10

<210> SEQ ID NO 43
<211> LENGTH: 9
<212> TYPE: PRT
<213> ORGANISM: Homo sapiens

<400> SEQUENCE: 43

Tyr Leu Asp Tyr Leu Arg Arg Arg Val
1               5

<210> SEQ ID NO 44
<211> LENGTH: 10
<212> TYPE: PRT
<213> ORGANISM: Homo sapiens

<400> SEQUENCE: 44

Ile Met Thr Arg Gly Asn Ala Lys Tyr Ala
1               5                   10

<210> SEQ ID NO 45
<211> LENGTH: 9
<212> TYPE: PRT
<213> ORGANISM: Homo sapiens

<400> SEQUENCE: 45

Asn Met Trp Leu Glu Tyr Tyr Asn Leu
1               5

<210> SEQ ID NO 46
<211> LENGTH: 10
<212> TYPE: PRT
<213> ORGANISM: Homo sapiens

<400> SEQUENCE: 46

Val Leu His Asp Ser Ser Lys Asp Ser Ile
1               5                   10

<210> SEQ ID NO 47
<211> LENGTH: 9
<212> TYPE: PRT
<213> ORGANISM: Homo sapiens

<400> SEQUENCE: 47

Ser Ile Thr Val Phe Val Ser Asn Leu
1               5

<210> SEQ ID NO 48
<211> LENGTH: 9
<212> TYPE: PRT
<213> ORGANISM: Homo sapiens

<400> SEQUENCE: 48

Ser Met Gln Glu Pro Asp Thr Lys Leu
1               5

<210> SEQ ID NO 49
<211> LENGTH: 10
<212> TYPE: PRT
<213> ORGANISM: Homo sapiens

<400> SEQUENCE: 49

Lys Ser Val Glu Gly Arg Pro Met Phe Val
1               5                   10

<210> SEQ ID NO 50
<211> LENGTH: 9
<212> TYPE: PRT
<213> ORGANISM: Homo sapiens

<400> SEQUENCE: 50

Lys Val Phe Arg Tyr Ser Thr Ser Leu
1               5

<210> SEQ ID NO 51
<211> LENGTH: 9
<212> TYPE: PRT
<213> ORGANISM: Homo sapiens

<400> SEQUENCE: 51

Met Leu Leu Pro Gln Thr Tyr Gly Ala
1               5

<210> SEQ ID NO 52
<211> LENGTH: 10
<212> TYPE: PRT
<213> ORGANISM: Homo sapiens

<400> SEQUENCE: 52

Lys Met Ser Asn Ala Asp Phe Ala Lys Leu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Variant of SEQ ID NO:3
<221> NAME/KEY: misc_feature
<222> LOCATION: (2)..(2)
<223> OTHER INFORMATION: Xaa can be Phe, Tyr, Met or Trp
<221> NAME/KEY: misc_feature
<222> LOCATION: (10)..(10)
<223> OTHER INFORMATION: Xaa can be Phe, Leu, Ile, Trp or Met

<400> SEQUENCE: 53

Val Xaa Asp Tyr Asn Cys His Val Asp Xaa
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Variant of SEQ ID NO:4
<221> NAME/KEY: misc_feature
<222> LOCATION: (2)..(2)
<223> OTHER INFORMATION: Xaa can be Phe, Tyr, Met or Trp
<221> NAME/KEY: misc_feature
<222> LOCATION: (10)..(10)
<223> OTHER INFORMATION: Xaa can be Phe, Leu, Ile, Trp or Met

<400> SEQUENCE: 54

Leu Xaa Glu Lys Ala Val Lys Asp Tyr Xaa
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Variant of SEQ ID NO: 5
<221> NAME/KEY: misc_feature
<222> LOCATION: (2)..(2)
<223> OTHER INFORMATION: Xaa can be Phe, Tyr, Met, or Trp
<221> NAME/KEY: misc_feature
<222> LOCATION: (9)..(9)
<223> OTHER INFORMATION: Xaa can be Phe, Leu, Ile, Met, or Trp

<400> SEQUENCE: 55

Asn Xaa Asn Lys Ala Leu Gln Gln Xaa
1               5

<210> SEQ ID NO 56
<211> LENGTH: 9
<212> TYPE: PRT
<213> ORGANISM: Artificial Sequence
<220> FEATURE:
<223> OTHER INFORMATION: Variant of SEQ ID NO: 6
<221> NAME/KEY: misc_feature
<222> LOCATION: (2)..(2)
<223> OTHER INFORMATION: Xaa can be Phe, Tyr, Met, or Trp
<221> NAME/KEY: misc_feature
<222> LOCATION: (9)..(9)
<223> OTHER INFORMATION: Xaa can be Phe, Leu, Ile, Met, or Trp

<400> SEQUENCE: 56

Ala Xaa Ile Asp Phe Glu Met Lys Xaa
1               5

<210> SEQ ID NO 57
<211> LENGTH: 10
<212> TYPE: PRT
<213> ORGANISM: Artificial Sequence
<220> FEATURE:
<223> OTHER INFORMATION: Variant of SEQ ID NO: 7
<221> NAME/KEY: misc_feature
<222> LOCATION: (2)..(2)
<223> OTHER INFORMATION: Xaa can be Phe, Tyr, Met, or Trp
<221> NAME/KEY: misc_feature
<222> LOCATION: (10)..(10)
<223> OTHER INFORMATION: Xaa can be Phe, Leu, Ile, Met, or Trp

<400> SEQUENCE: 57

Asp Xaa Val Glu Ile Trp Gln Ala Tyr Xaa
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Variant of SEQ ID NO: 8
<221> NAME/KEY: misc_feature
<222> LOCATION: (2)..(2)
<223> OTHER INFORMATION: Xaa can be Phe, Tyr, Met, or Trp
<221> NAME/KEY: misc_feature
<222> LOCATION: (9)..(9)
<223> OTHER INFORMATION: Xaa can be Phe, Leu, Ile, Met, or Trp

<400> SEQUENCE: 58

Asp Xaa Leu Arg Arg Arg Val Asp Xaa

```
<210> SEQ ID NO 59
<211> LENGTH: 9
<212> TYPE: PRT
<213> ORGANISM: Artificial Sequence
<220> FEATURE:
<223> OTHER INFORMATION: Variant of SEQ ID NO: 9
<221> NAME/KEY: misc_feature
<222> LOCATION: (2)..(2)
<223> OTHER INFORMATION: Xaa can be Phe, Tyr, Met, or Trp
<221> NAME/KEY: misc_feature
<222> LOCATION: (9)..(9)
<223> OTHER INFORMATION: Xaa can be Phe, Leu, Ile, Met, or Trp

<400> SEQUENCE: 59

Ala Xaa Thr Arg Ala Leu Glu Tyr Xaa
1               5

<210> SEQ ID NO 60
<211> LENGTH: 9
<212> TYPE: PRT
<213> ORGANISM: Artificial Sequence
<220> FEATURE:
<223> OTHER INFORMATION: Variant of SEQ ID NO: 25
<221> NAME/KEY: misc_feature
<222> LOCATION: (9)..(9)
<223> OTHER INFORMATION: Xaa can be Val or Leu
<221> NAME/KEY: misc_feature
<222> LOCATION: (2)..(2)
<223> OTHER INFORMATION: Xaa can be Leu, Met, Val, Ile or Gln

<400> SEQUENCE: 60

Trp Xaa His Asp Glu Ile Ser Met Xaa
1               5

<210> SEQ ID NO 61
<211> LENGTH: 9
<212> TYPE: PRT
<213> ORGANISM: Artificial Sequence
<220> FEATURE:
<223> OTHER INFORMATION: Variant of SEQ ID NO: 26
<221> NAME/KEY: misc_feature
<222> LOCATION: (2)..(2)
<223> OTHER INFORMATION: Xaa can be Leu, Met, Val, Ile or Gln
<221> NAME/KEY: misc_feature
<222> LOCATION: (9)..(9)
<223> OTHER INFORMATION: Xaa can be Val or Leu

<400> SEQUENCE: 61

Ser Xaa Phe Arg Arg Gln Leu Ala Xaa
1               5

<210> SEQ ID NO 62
<211> LENGTH: 9
<212> TYPE: PRT
<213> ORGANISM: Artificial Sequence
<220> FEATURE:
<223> OTHER INFORMATION: Variant of SEQ ID NO: 27
<221> NAME/KEY: misc_feature
<222> LOCATION: (2)..(2)
<223> OTHER INFORMATION: Xaa can be Leu, Met, Val, Ile or Gln
<221> NAME/KEY: misc_feature
<222> LOCATION: (9)..(9)
<223> OTHER INFORMATION: Xaa can be Leu or Val

<400> SEQUENCE: 62

Leu Xaa Gln Ala Glu Ala Pro Arg Xaa
1               5

<210> SEQ ID NO 63
```

```
-continued

<211> LENGTH: 9
<212> TYPE: PRT
<213> ORGANISM: Artificial Sequence
<220> FEATURE:
<223> OTHER INFORMATION: Variant of SEQ ID NO: 28
<221> NAME/KEY: misc_feature
<222> LOCATION: (2)..(2)
<223> OTHER INFORMATION: Xaa can be Leu, Met, Val, Ile or Gln
<221> NAME/KEY: misc_feature
<222> LOCATION: (9)..(9)
<223> OTHER INFORMATION: Xaa can be Leu or Val

<400> SEQUENCE: 63

Arg Xaa Ala Glu Tyr Gln Ala Tyr Xaa
1               5

<210> SEQ ID NO 64
<211> LENGTH: 9
<212> TYPE: PRT
<213> ORGANISM: Artificial Sequence
<220> FEATURE:
<223> OTHER INFORMATION: Variant of SEQ ID NO: 29
<221> NAME/KEY: misc_feature
<222> LOCATION: (2)..(2)
<223> OTHER INFORMATION: Xaa can be Leu, Met, Val, Ile or Gln
<221> NAME/KEY: misc_feature
<222> LOCATION: (9)..(9)
<223> OTHER INFORMATION: Xaa can be Leu or Val

<400> SEQUENCE: 64

Leu Xaa Ala Met Glu Arg His Gly Xaa
1               5
```